US006249784B1

United States Patent
Macke et al.

(10) Patent No.: US 6,249,784 B1
(45) Date of Patent: Jun. 19, 2001

(54) SYSTEM AND METHOD FOR SEARCHING AND PROCESSING DATABASES COMPRISING NAMED ANNOTATED TEXT STRINGS

(75) Inventors: Thomas J. Macke, Las Vegas, NV (US); Bill F. Butler, La Jolla; James P. O'Connell, Solana Beach, both of CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/315,592

(22) Filed: May 19, 1999

(51) Int. Cl.$^7$ ...................................................... G06F 17/30
(52) U.S. Cl. ........................................................... 707/3
(58) Field of Search ......................................... 707/1, 2, 3

(56) References Cited

U.S. PATENT DOCUMENTS

| | | | |
|---|---|---|---|
| 5,392,428 | * | 2/1995 | Robins .................................... 707/3 |
| 5,404,295 | * | 4/1995 | Katz et al. .............................. 707/2 |
| 6,006,217 | * | 12/1999 | Lumsden ................................. 707/2 |

OTHER PUBLICATIONS

Stevens, A. "Building the Text Engine Database", Dr Dobbs's Journal, Feb. 1995, vol. 20, No. 2, p. 199(6).*

* cited by examiner

*Primary Examiner*—Jack Choules
(74) *Attorney, Agent, or Firm*—Lyon & Lyon LLP

(57) ABSTRACT

A system and method for processing, searching, and performing in-context searches on named annotated text string databases. The system and method provides users with a means for interactively refining database searches in order to account for differences in keywords used to describe similar phenomena. The system and method provides a means for performing searches for particular predefined target strings in context of particular predefined context strings. Data is represented using data types referred to as Hits and E-Hits. Hits data contains locations of search results and the E-Hits data contains text of search results. Hits lists are sorted and duplicate entries are discarded. Context search results are segregated from non-context search results by sorting the Hits lists. The Search module operates on a Hits list and selects those elements that match one or more search key(s). The output from a Search module is a Results Hits list. The Context Search module accepts two inputs in addition to the search key(s), a Context Hits list and a Target Hits list. The output of the Context Search module is a Hits list that contains matches found within the specified context. The Select module accepts a stream of Hits as input parameters and can be used to add or subtract annotations to the results of a search, remove base text sub-strings from the results of a search, or perform additional processing on Hits that may be useful for context searching. The Extract module is used to extract actual data from a Hits list, typically for display to a user and/or for converting results to keywords used for a subsequent search.

26 Claims, 19 Drawing Sheets

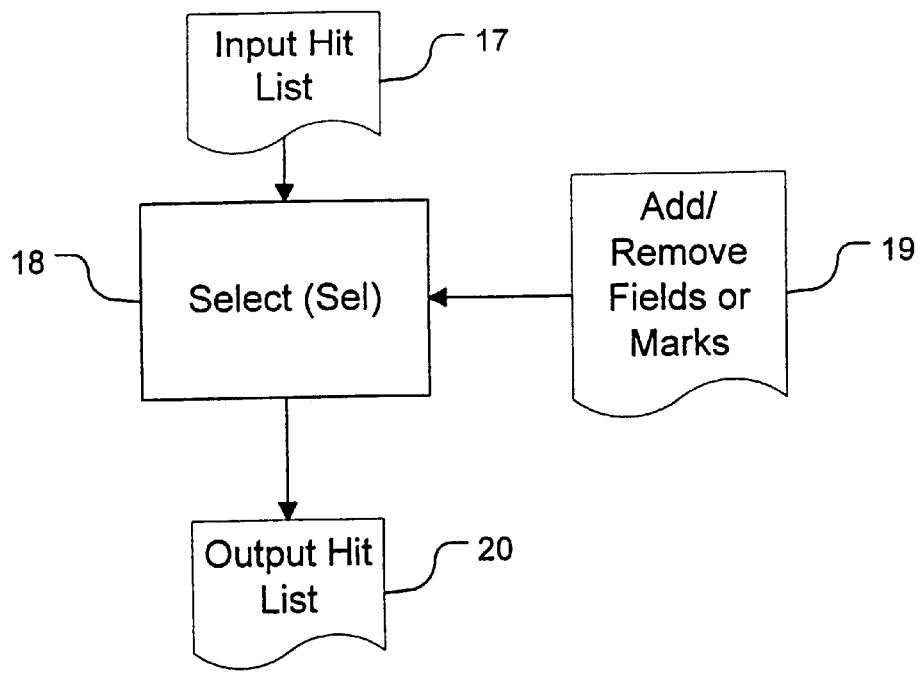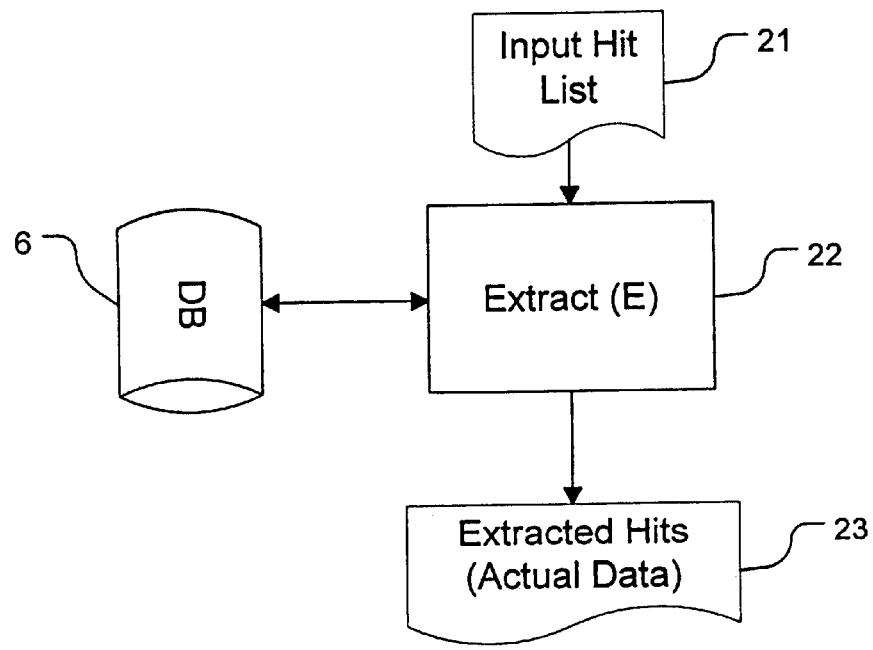
Fig. 4

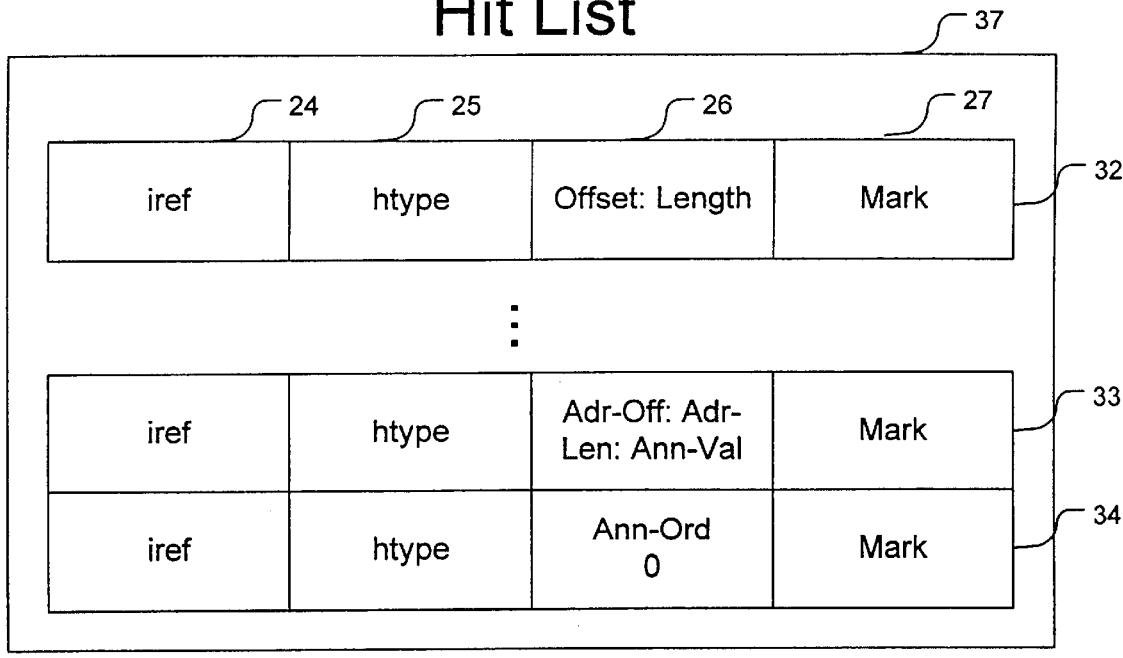
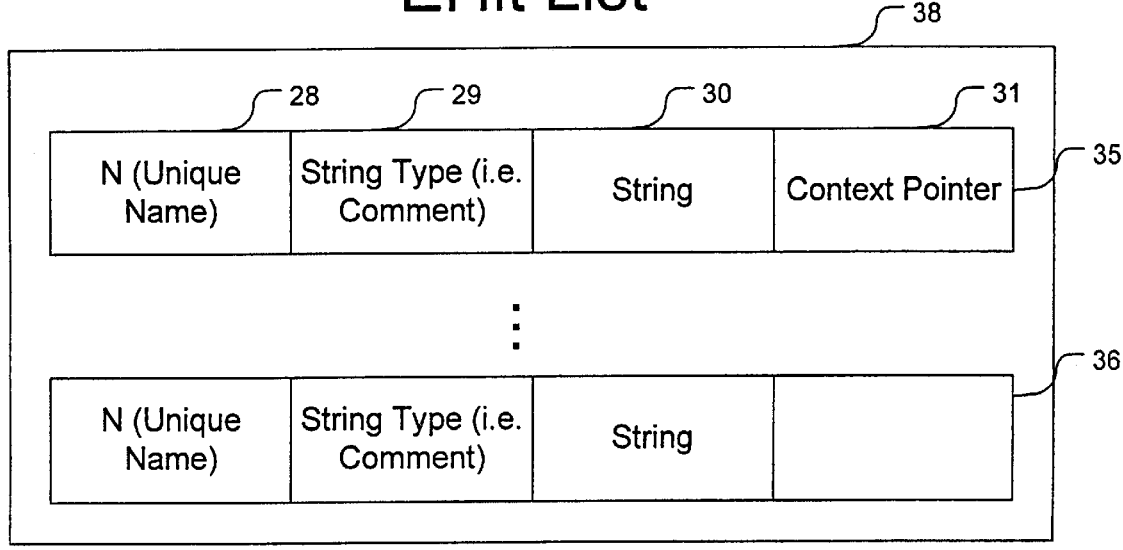
Fig. 5

```
                    Column 1   Column 12                                              Column 79

40 ─── LOCUS       ANANIFDR2       293 bp    DNA              BCT       08-NOV-1993
41 ─── DEFINITION  A.variabilis nifD gene 3' recombination site, and xisA gene, 5'
                   end.
42 ─── ACCESSION   M28153
43 ─── NID         g142043
44 ─── VERSION     M28153.1  GI:142043
45 ─── KEYWORDS    nifD gene; nitrogenase; xisA gene.
46 ─── SEGMENT     2 of 2
47 ─── SOURCE      Anabaena variabilis (strain ATCC 29413) vegetative cell DNA, cosmid
                   33D12.
60 ───   ORGANISM  Anabaena variabilis
67 ───             Eubacteria; Cyanobacteria; Nostocales; Nostocaceae; Anabaena.
48 ─── REFERENCE   1  (bases 1 to 10; 277 to 293)
61 ───   AUTHORS   Brusca,J.S.
62 ───   JOURNAL   Unpublished (1989)
49 ─── REFERENCE   2  (bases 11 to 276)
63 ───   AUTHORS   Brusca,J.S., Hale,M.A., Carrasco,C.D. and Golden,J.W.
64 ───   TITLE     Excision of an 11-kilobase-pair DNA element from within the nifD
                   gene in Anabaena variabilis heterocysts
65 ───   JOURNAL   J. Bacteriol. 171, 4138-4145 (1989)
66 ───   MEDLINE   89327123
```

Fig. 6A

```
COMMENT       Draft entry and computer-readable sequence for [2],[1] kindly
              submitted by J.S.Brusca, 19-SEP-1989.
              Base pairs 261 to 293 are part of coding sequence for the nifD gene
              which is non-functional in the vegetative cell.  Base pairs 1 to
              260 are the end of the 11-kilobase-pair element which is excised
              from the chromosome during heterocyst differentiation to produce a
              functional nifD gene.  Base pairs 250 to 260 form an 11-bp direct
              repeat which flanks the 11-kb element.
              See GenBank accession numbers M29073 and M29074 for sequences of
              recombined nifD gene and excised circular DNA.
FEATURES             Location/Qualifiers
     source          1..293
                     /organism="Anabaena variabilis"
                     /db_xref="taxon:1172"
     CDS             complement(<1..128)
                     /note="xisA peptide A (alt.)"
                     /codon_start=1
                     /transl_table=11
                     /protein_id="AAA22010.1"
                     /db_xref="PID:g142045"
                     /db_xref="GI:142045"
                     /translation="QNQGQDKYQQAFADLEPLSSTDGSFLGSSLQAQQQREHMRTKV"
BASE COUNT      77 a     62 c     59 g     95 t
ORIGIN      About 10.7 kb after segment 1.
        1 actttgttc tcatgtgttc tcttgctgc tgtgcttgca gacttgagcc gagaaaactg
       61 ccgtcggtag atgaaagtgg ctccaagtct gcaaaggctt gttgatattt gtcttgaccc
      121 tgattttgca tcgctgtggt attagcctat attagccta aaaattaatg tgtttatcagc
      181 aaacaatgtt catcactaac actgctcagt gcaaacatta agctgttgaa agctattaaa
      241 ccacaaaaag gattactccg gcccttatca cggttacgac ggatttgcta tct
```

Fig. 6B

159 Sequence File

| LOCUS ANANIFDR2 293 bp DNA BCT 08-NOV-1993 DEFINITION... |

160 Index File

| Offset into sequence file | Length of locus | Offset into PSKEL file | Length of PSKEL entry |

162     163     164     165

170 PSKEL File 171   172   173

Single PSKEL Entry:

| Searchable Object Name | Offset | Length |
| --- | --- | --- |
| Locus | 0 | 72 |
| Definition | 73 | 96 |
| ⋮ | | ⋮ |
| Sequence | 1029 | 20021 |

Search Hits [1,S] 230

| | IREF | Type | Mark |
|---|---|---|---|
| 360 | 420 | Chk | 0 |
| 361 | 422 | Chk | 0 |
| 362 | 423 | Chk | 0 |
| 363 | 424 | Chk | 0 |
| 364 | 425 | Chk | 0 |

Mark Hits: (1, M) 231

| | IREF | Type | Mark |
|---|---|---|---|
| 98 | 417 | X | 0 |
| 99 | 423 | CDS 1 | 0 |
| 100 | 423 | CDS 2 | 0 |
| 101 | 423 | CDS 3 | 0 |
| 102 | 452 | X | 0 |

*Fig. 15*

Mark Hits: (1, M) — 211

|     | IREF | Type | Mark |
|-----|------|------|------|
| 98  | 417  | X    | 0    |
| 99  | 423  | CDS1 | 0    |
| 100 | 423  | CDS2 | 0    |
| 101 | 423  | CDS3 | 0    |
| 102 | 452  | X    | 0    |

Result Hits [1,RP] (Preliminary) — 265

|     | IREF | Type | Mark |
|-----|------|------|------|
| 216 | 417  | X    | X    |
| 217 | 423  | tfbs | 99   |
| 218 | 423  | tfbs | 100  |
| 219 | 423  | tfbs | 100  |
| 220 | 487  | X    | X    |

Result Hits [1,RM] (Merged) — 270

|     | IREF | Type | Mark |
|-----|------|------|------|
| 176 | 389  | X    | X    |
| 177 | 423  | CDS1 | 0    |
| 178 | 423  | CDS2 | 0    |
| 179 | 423  | tfbs | 177  |
| 180 | 487  | tfbs | 178  |
| 181 | 487  | tfbs | 178  |
| 182 | 502  | X    | X    |

*Fig. 18*

SYSTEM AND METHOD FOR SEARCHING AND PROCESSING DATABASES COMPRISING NAMED ANNOTATED TEXT STRINGS

BACKGROUND OF THE INVENTION

1. Field of the Invention

The present invention relates generally to database processing, and more particularly to a system and method for efficiently searching and extracting relevant data, and for performing contextual data searches on databases comprising named annotated text strings, such as biological sequence databases.

2. Related Art

For nearly thirty years, scientists have been collecting biological sequence data on different types of organisms, ranging from bacteria to human beings. Much of the data collected is stored in one or more databases shared by scientists around the world. For example, a genetic sequence database referred to as the European Molecular Biology Lab (EMBL) gene bank is maintained in Germany. Another example of a genetic sequence database is Genbank, and is maintained by the United States Government.

Specifically, Genbank is a public nucleic acid sequence database operated by the National Center for Biotechnology Information (NCBI), a part of the National Library of Medicine (NLM) which is itself a part of the National Institutes of Health (NIH). Currently, the Genbank database may be queried using NCBI's Website (www.ncbi.nlm.nih.gov) or can be accessed through one of several specialized NCBI e-mail servers. Additionally, the Genbank database may be downloaded either in its entirety or in part from NCBI's anonymous FTP server.

Genbank is compiled from international sources and currently comprises sequence data in the following 13 categories: "primate," "mammal," "rodent," "vertebrate," "invertebrate," "organelle," "RNA," "bacteria," "plant," "virus," "bacteriophage," "synthetic," and "other". Genbank is logically organized as 17 sub-databases sharing a common naming convention and schema. These sub-databases correspond roughly to the major research organisms listed above, derived sequences such as plasmids and patented sequences, and sequences that are produced by the various complete genome projects.

The potential benefits gained by studying genetic sequences and understanding genetic coding are boundless. For example, such understanding can lead to discovery of genes that affect incidences and the severity of diseases. Understanding genetic sequences can lead to diagnosis, treatment and prevention of genetic diseases and the design of drugs that can specifically target critical protein sites. In addition, studying genetic sequences facilitates our understanding of evolutionary biology.

The Human Genome Project (HGP) is an international research program carried out in the United States by the National Human Genome Research Institute and the US Department of Energy. The ultimate task of sequencing all 3 billion base pairs in the human genome will provide scientists with a virtual instruction book for a human being. From there, researchers can begin to unravel biology's most complicated processes.

The problem is that such enormous undertakings necessarily generate huge and ever-increasing amounts of data. Databases such as Genbank facilitate the process of organizing and disseminating such data to scientists around the world. However, it has proven to be extremely challenging not only to manage and disseminate the data, but more importantly, to perform meaningful analysis on such voluminous databases. The data analysis problem is due is part, to the format of the data provided by databases such as Genbank.

The Genbank database and other similar databases comprise a set of named annotated text strings (NAT). The so-called "text string" portion of the Genbank and other biological databases is the actual recorded sequence data. The annotations comprise documented information about the sequence data or portions thereof. Each element or entry has a unique name. Such databases are inherently difficult to process using conventional database query languages, such as SQL and the like.

Currently, the version of the Genbank database available through their FTP Website consists of a set of individual files. Each file contains sequences from a single sub-database, which may itself comprise multiple files. The partitioning of Genbank in this fashion allows investigators to load (and search) only as much or as little of the database as they require. This has proven to be quite an advantage as the current Genbank release (release 111.0, April 1999), contains over 3.5 million entries ("loci") and requires about 7.5 GB of (uncompressed) disk space.

However, performing meaningful data analysis on the voluminous Genbank database and other similar databases has proven to be extremely problematic. This is due to many factors, including the complexity, the data format, and the shear size of the data itself. Such data is very difficult to analyze using conventional means. In addition, because these databases have been in place for so many years, and are shared by scientists throughout the world, it is difficult to incorporate changes, even if such changes are advantageous to researchers.

Thus, at least for the foreseeable future, researchers must continue to deal with such data in much the same format as is currently implemented. The difficult-to-work-with nature is unavoidable due to many factors as listed above, but also because our understanding of the sequences is incomplete and often incorrect.

Further, there is no standard vocabulary by which the entries are described. For example, comments and notes are typically entered by researchers in plain text, which is generally unrestricted as to its format. For example, suppose a researcher conducts a search for bacteria sequences that are resistant to antibiotics. This search would be trivial if all researchers were restricted to particular keyword description for this particular characteristic, such as "antibiotic resist" or the like. However, because no restrictions are enforced, some researchers describe this phenomena with different terms such as "antibiotic resist," "penicillin resistance," "beta-lactamase" and the like.

In addition, it would be desirable and very valuable to conduct searches for certain sequences that are in context of other sequences. This is a very difficult problem that has thus far remained unresolved using current systems.

Therefore, what is needed is a system and method that can operate on named annotated string databases such as biological sequence databases, in an efficient and meaningful manner. Further, what is needed is a system and method that can perform in-context database searches on named annotated text string databases.

SUMMARY OF THE INVENTION

Accordingly, the present invention is directed toward a system and method for processing and searching named annotated text string databases, such as biological sequence databases, in a fast and efficient manner. Further, the present invention provides a system and method for performing in-context searches on named annotated text string databases in a fast and efficient manner.

The data mining aspect of the present invention provides users with a means for interactively refining database searches in order to account for differences in the description of similar phenomena. In particular, the present invention provides users with a means for interactively editing search results and automatically converting those results into search keys that are used to conduct one or more subsequent searches. This aspect of the present invention solves the problem caused by using inconsistent keywords.

The context-searching aspect of the present invention provides users with the ability to search for particular predefined target strings in context of particular predefined context strings. This includes strings that are implicitly referenced in the annotation section of such databases. For example, the present invention can be used to search for particular predefined target strings that are within a predefined distance, upstream or downstream, of predefined context strings.

The present invention can be used with any type of database comprising named annotated text strings (NATs). Two specialized data types, referred to as Hits and E-Hits are used to represent data in accordance with the present invention. Hits data contains the locations of the search results and E-Hits data contains the text of the search results. The Hits data type is used to pass intermediate search results through a network of functional components that perform specific database search operations, such as search, context search, select and extract. The E-Hits data type is used to display results. Further, the E-Hits data is used to present results to the user for line-oriented text processing and further data analysis.

The results of a search are a finite stream of Hits referred to a "Hits list" or "Hits table." In a Hits list, Hits are numbered consecutively and each Hit represents a match to a particular search key. The Hits data type is extremely efficient because it comprises a single multiple-digit mixed radix identifying number.

In one embodiment, the most significant digit of the Hits data is an index into a zero-based array that contains the unique names of all of the elements (i.e. entries) in the NAT database. The second digit specifies whether the search result is an annotation or part of the base text. The third digit identifies the particular annotation or sub-string of the base text and may comprise more than one number, depending on the type of entry identified by the second digit. The forth digit comprises information associated with in-context searches. In particular, if a search is the result of a context search, the forth digit comprises an index into a Hits list that describes the context for the search result.

A Hits list is sorted and duplicate entries are discarded. This feature provides the advantage of quickly eliminating redundant results due to searches using multiple terms. The ordering of Hits lists is also used to a great advantage in context searches. In particular, the Hits lists are quickly sorted such that the context search results are easily segregated from the non-context search results. Accordingly, all Hits include another digit of a radix larger than the cardinality of the largest expected Hits stream.

An E-Hit is a printable text representation of the actual string value referenced in the corresponding Hit. E-Hits are used for text processing, such as formatting for a display screen or printout on a printer. Further, E-Hits are also used for analysis by users. For example, E-Hits are used in line-oriented text processing for converting search results into keywords for subsequent searches. Each E-Hit is preferably a single line of text comprising multiple tab-separated fields. A stream of E-Hits is thus a stream of text lines that have a one to one correspondence with an associated stream of Hits.

Four specific function modules are provided by the present invention. These modules are referred to as the Search module, the Context Search module, the Extract module and the Select module.

The Search module operates on a Hits list and selects those elements that match one or more search key(s). The result of a Search module is a Results Hits list that contains pointers to the matched data.

The Context Search module is a variation of the Search module, but accepts two inputs, rather than one, in addition to the search key(s). The first input is a Hits list representing context strings. The second input is a Hits list containing target strings. The output of the Context Search module is a Hits list that contains matches found within the specified context.

The Select module accepts a stream of Hits as input parameters. The Select module can be used to add or subtract annotations to the results of a search. In addition, the Select module can be used to remove base text sub-strings from the results of a search. Still further, the Select module can be used to perform additional processing on Hits that may be useful for context searching.

The Extract module is used to extract actual data from a Hits list. Typically, this is used to display actual data to a user for viewing the results of a search. For example, in one embodiment, the Extract module is used to display search results to a user on a display screen so that the user can edit results and select particular keywords therefrom to be used in a subsequent search.

BRIEF DESCRIPTION OF THE FIGURES

The present invention is described with reference to the accompanying drawings, wherein:

In the figures, like reference numbers generally indicate identical, functionally similar, and/or structurally similar elements.

FIG. 4 is a block diagram depicting a Select and Extract module and their associated inputs and outputs, in accordance with an embodiment of the present invention.

FIG. 5 is a block diagram depicting the structure of a Hit list and an E-Hit list, in accordance with an embodiment of the present invention.

FIGS. 6A and 6B is an example of an entry from a Genbank genetic database.

FIGS. 12 and 13 are block diagrams depicting various data structures in accordance with an embodiment of the present invention.

FIG. 15 is a block diagram depicting Hit tables that can be used to implement a context search in accordance with an embodiment of the present invention.

FIG. 18 is a block diagram depicting Hit tables that can be used to implement a context search in accordance with an embodiment of the present invention.

DETAILED DESCRIPTION OF THE PREFERRED EMBODIMENTS

The present invention can be used with any type of database comprising "named annotated text strings" (NAT). In the description below, the present invention is described in general terms using a generic NAT dataset. This description is followed by a detailed description of a specific embodiment of the present invention using the Genbank database.

An NAT database comprises a set (S) of named annotated text strings. Each element of this set comprises a set defined as {N,A,T}, where "N" is a character string that represents the element's unique name. "T" is referred to as the base text and comprises a text string (which can be any length) to which the annotations apply. "A" is the set of annotations that apply to "T". Each annotation is also a set containing another text string that is the actual annotation. An optional address that specifies the characters of the base text string to which the annotation applies may also be present. An annotation may also comprise an optional type, which is another short text string that governs the meaning of the annotation's text.

Figure 1:
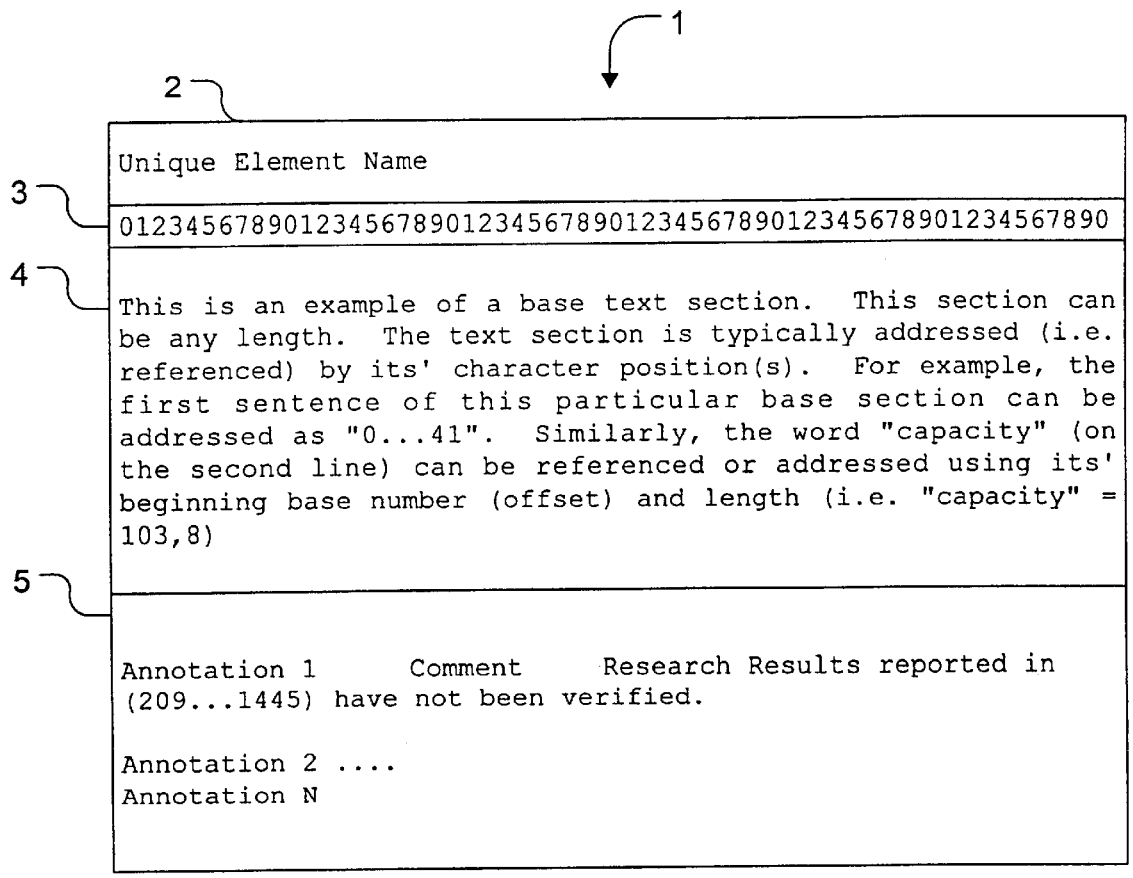
FIG. 1 is a diagram depicting the elements of a generic named annotated text string (NAT) database, in accordance with an embodiment of the present invention.

An example of a single element or entry in a NAT dataset is shown in FIG. 1. The entry 1 comprises a unique element name (N)2, a base text (T) section 4, and an annotation (A) section 5. As described below, the T section 4 can be addressed or referenced by its' character position(s). The character position section 3 is added to FIG. 1 to aid in the description below and is not typically present in the database entry 1.

Annotations 5 can apply to a specific T section 4 "address." Those annotations 5 that do not specify an address generally apply to the entire base text section 4. Annotations without an explicit type are assigned a special type of "untyped". Type strings are typically context free. Generally, all uses of a type string, in a single NAT dataset specify the same type. All annotations are distinct. This is, no two annotations have the same type, address and value.

Referring back now to FIG. 1, the first annotation labeled "Annotation 1" depicts an example of a base T 4 address. In this example, a comment is made in reference to a specific portion of the T section 4 that begins in character position 209 and ends in character position 1445.

Another example of T section 4 addressing is depicted in the T 4 section itself. As stated, the T 4 section can be of any length (restricted by storage capacity and performance considerations, etc.). Generally, the T 4 section is quite large. As stated, the T 4 section can be referenced by any of the annotations in section 5. The T 4 section is typically addressed by its' character position(s), however, other means for addressing can be applied to alternative embodiments of the present invention.

For example, the first sentence (including the period) of this particular base section 4 can be addressed as "0 ... 41". Similarly, the sub-string "capacity" (on the second line) can be referenced or addressed using its' beginning base number (offset) and length (i.e. "capacity"=103,8).

Searches are performed using search functions that operate in accordance with the principals described below. It is noted that these search functions are described below in terms of four separate functional modules. These modules are referred to as search (S), select (SEL), context search (CS) and extract hits (E). The use of four modules to describe these functions are for exemplary purposes only to distinctly point out and describe the details of the present invention. In other embodiments, many different organizations are possible. Accordingly, the use of these examples should not be construed to limit the scope and breadth of the present invention.

Each module performs a specific well-defined step of a search. Complex searches are preferably performed by connecting two or more of the functional modules in a computational network. An example of a computational network is described below.

Preferably, two data types are used to represent the NAT dataset in accordance with a preferred embodiment of the present invention. These data types are referred to as Hits and E-Hits and are described in detail below. Briefly however, Hits contain the locations (i.e. pointers) to the search results and E-Hits contain the actual text or strings associated with the search results. An array or stream of Hits is referred to herein as a "Hits list" or "Hits table." Similarly, an array or stream of E-Hits is referred to herein as an "E-Hits list" or "E-Hits table."

Figure 2:
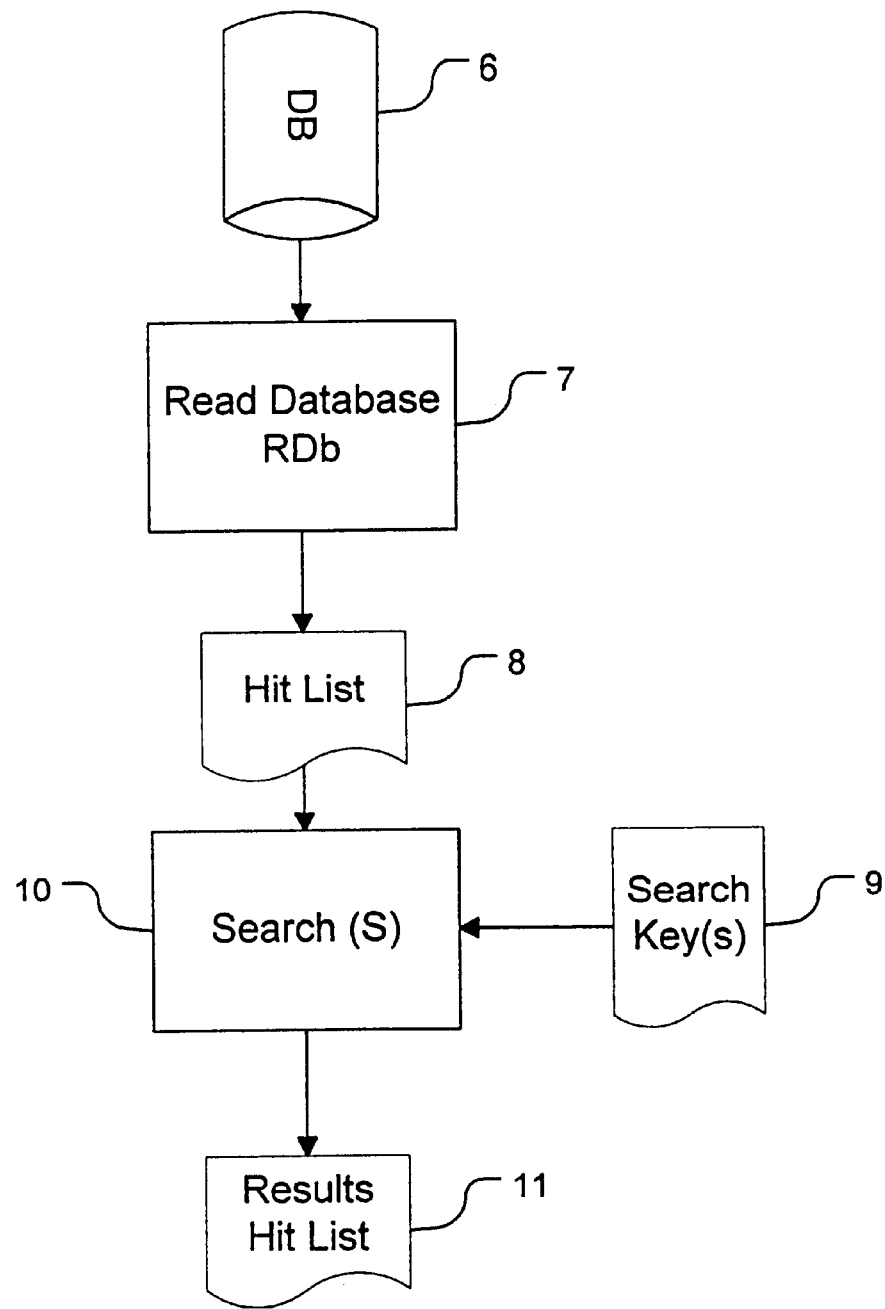
FIG. 2 is a block diagram depicting a Search module and its associated inputs and outputs, in accordance with an embodiment of the present invention.

FIG. 2 is a block diagram depicting a Search module that shows a typical example of input and output streams, in accordance with an embodiment of the present invention. The NAT dataset 6 is input into a read database module 7. The output of a read database module 7 is the dataset 6 (or portion thereof), in the form of a Hits list 8, as described below. The Search module operates on the Hits list 8 and selects those elements of the original dataset 6 that match the search key(s) 9. Both the annotations 5 and the base text 4 can be searched using the Search module 10. The selected results 11 are returned as a new stream of Hits or Hits list 11.

Specifically, the Search module 10 functions as the basic (non-context) search algorithm. The Search module 10 accepts three inputs: (1) a Hits list 8 to check for matches, referred to as "Search Hits", a list of search keys 9, and a function that is used to test if a search key matches the text referenced by each Search Hit (not shown). Each element of the Search Hits list 8 refers to either a specific annotation 5 of one element of the NAT dataset being searched, or to a specific sub-string of the base text 4 of one element of the NAT dataset being searched. The Search algorithm 10 uses this reference to load the actual object to be tested against the search key(s) 9 into memory. If it matches, the process adds the Hit corresponding to this match to the preliminary Result Hits table (not shown, described below). After all Hits have been tested against all search keys 9, the Result Hits table 11 is sorted and duplicate entries are removed. This non-redundant Result Hits table 11 is the output of Algorithm S 10.

The initial input to Algorithm S 10 is a Search Hits table 8 that contains an entry for every searchable entity in the NAT dataset under examination with one exception. This exception is for the base text 4 of each element of the NAT dataset. This is because every sub-string of an element's base text is contained in that base text 4, so the initial input Hits table 8 contains only one reference to an element's base text 4. Specifically, a sub-string of length L beginning at offset 0, which represents the entire base text section 4.

Figure 3:
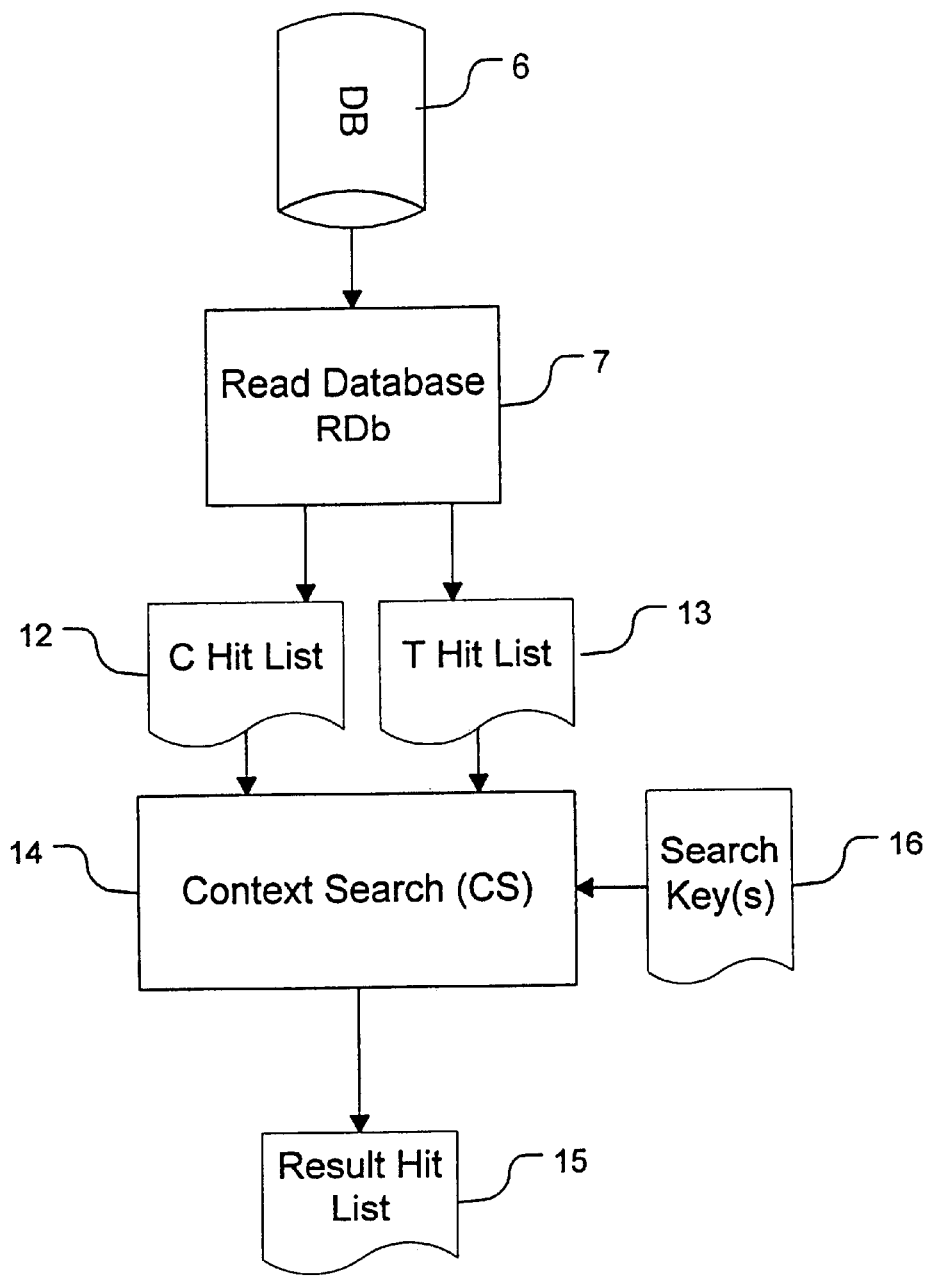
FIG. 3 is a block diagram depicting a Context Search module and its associated inputs and outputs, in accordance with an embodiment of the present invention.

FIG. 3 is a block diagram depicting a context Search module (CS) 14 and typical input and output streams, in accordance with an embodiment of the present invention. Again, the NAT dataset 6 is input into a read database module 7. The output of a read database module 7 is a dataset (or portion thereof), in the form of a context Hits list 12. The context Hits list 12 is a Hits list that is to be used to describe the context for the search performed by the CS module 14.

An additional Hits list, referred to as a target Hits list 13, is also used as input to the CS 14 module. In this example, the target Hits list 13 is shown as a Hits list from the original database 6. This however, is just one example of a target Hits list. In another example, as described below, the target Hits list 13 is compiled separately from another source that is different from the database 6. In any case, however, the two inputs to the CS module 14 are separate Hits lists, one that describes the target search strings 13 and another 12 that describes the context in which to search for the target strings.

In this example, the search keys 16 are used to describe the relationship between the context Hits list 12 and the target Hits list 13 in which to perform the search. For example, one may wish to search for particular targets 13 that are within a particular distance (i.e. a particular number of bases upstream and/or downstream) from particular target (s) 13. The selected results of the context search are returned as a new stream of Hits 15.

In one embodiment, module CS 14 is an extension of module S 10. In general, module CS 14 partitions the base text string of each element of NAT data 6 into contiguous sub-strings referred to as context and target. This partitioning information is provided to module CS 14 from the locations of the second input Hits stream 12. When module CS 14 operates it checks the context clause in the search key(s) 16 which specifies the acceptable positional relationships between target sub-strings 13 and context sub-strings 12 and searches only those target sub-strings that have an acceptable context. Because the partitioning mechanism is so general, computation networks of programs implementing modules S 10, Sel 18 (see below) and CS 14 can easily perform very complicated and difficult context searches.

FIG. 4 is a block diagram depicting a Select (Sel) module 18 and an extract (E) module 22, as well as their associated inputs and outputs in accordance with an embodiment of the present invention. The Select module 18 accepts a stream of Hits 17 as input parameters. The Select module 18 can be used to add or subtract related annotations 5 (having specified types) to the results of a search. In addition, the Select module 18 can be used to remove base text sub strings from the results of a search. Still further, the Select module 18 can be used to perform additional processing on Hits that may be useful for context searching as described above.

In particular, the Select module 18 is used to add or subtract, without searching, other annotations from the set of annotations of each selected element of the NAT dataset that was searched by Search module 10. Sel 18 has two inputs, a Hits table 17 referred to as the input Hits list and a set of annotation type/action pairs. The Sel module 18 has one output 20, another Hits table referred to as Output Hits list 20. Algorithm Sel 18 examines each entry in the Input Hits table 17, checks its annotation type, and depending on the action specified for the annotation type performs one of the following functions.

The Sel module 18 either copies the entry to the Output Hits table 20 "As is", or discards the entry. A third action "Add" can also be used to add all annotations of the specified type(s) to the Output Hits table 20 for those elements of the NAT dataset that are present in the Input Hits table 17.

The Extract (E) module 22 is used to extract actual data from a Hits list. Typically, this is used to display actual data to a user so that results can be viewed. For example, in one embodiment, the E module 23 is used to display search results to a user on a display screen. The user can then edit the display of search results and select particular keywords therefrom, to be used in performing a subsequent database search.

As stated, a preferred embodiment of the present invention represents data as either Hits and E-Hits. FIG. 5 depicts an example of the format of these two data types. Hits data elements, such as element 32, contain locations of the search results. E-Hits data elements, such as element 35, contain the actual text of the search results. Typically, Hits are used to pass intermediate search results through a network of programs that implement the S 10, CS 14, Sel 18 and E 22 modules as described above. E-Hits are used to display search results and for further analysis via line oriented text processing. As stated, the result of a search is a finite stream of Hits or a Hits list 37. Individual Hits, such as Hit element 32 are numbered consecutively beginning with 1. Each Hit 32 represents a match to a particular search key. The contents of the Hit elements, such as element 32, are a unique multi-digit mixed radix identifying number. The example below describes one way to construct such as number.

In this example, the first or most significant digit 24 is referred to as the "iref," and functions as an index into a zero-based array that contains the names of all the elements in the NAT dataset 6 sorted in lexical order. The radix of the first digit 24 must be at least one plus the index of the last number in this global index (described below). The value of this digit 24 identifies a particular {Name, Annotations, Text} element or entry in the NAT dataset 6.

The second digit 25, referred to as the "htype," is selected to specify whether the search result refers to an annotation 5 or a base text sub-string 4. For NAT datasets 6 containing only untyped annotations, this can implemented with a single binary bit. For example, if this bit is 0, the element refers to an annotation 5. Similarly, if the value is 1, the element refers to a string in the base text section 4.

More typically, however, some or all of the annotations in section 5 are explicitly typed. In this case the annotations are explicitly typed, with #t being the number of explicit types. Thus, the explicit types are numbered from 0 to #t−1. In this example, #t is used to indicated that the type of result is actually in the base text section 4.

If the annotations include a mixture of #t explicitly typed annotations and untyped annotations, the values #t and #t+1 can be used to indicate the annotation is untyped or in the base text section 4, respectively. The radix of this digit must be at least #t+1, for NAT datasets containing only typed annotations, and #t+2 for NAT datasets containing a mixture of typed and untyped annotations.

The next digit 26 may comprise one or more numbers, depending on the type of data the particular Hit element represents. This digit 26 identifies a particular annotations or a particular sub-string of the base text 4. The value of this radix 26 depends on the number of annotations 5 and the length the longest base text 4 in the dataset 6. It is important that the same number, radices and order of digits be used for both annotation and text sub-string results, so that all of the elements of an NAT dataset 6 use the same numbering scheme.

For example, one should consider the storage requirements for encoding any non-null sub-string of the base text 4 including the entire string. Typically, two numbers are required: the starting position or offset of the sub-string, and the length of the sub-string. Using this encoding scheme, text strings are numbered consecutively from 0 to L−1, where L is the length of the string.

The largest possible offset is L−1, which is used for a sub-string of length 1 beginning in the last character position of the text string 4. The longest length is L, which is used for the entire string 4. Because the same encoding is used for all elements of an NAT dataset 6, the radices that are used to hold the offsets and lengths of the selected sub-strings must be at 1 plus the length of the longest base text string in the entire NAT dataset 6.

Next one should consider storage requirements for encoding the annotations 5. Typically, a unique number is assigned to each possible type of annotation. This is possible because every annotation when considered as a set of {type, address, value} is unique. The second digit 25 of the encoding element stores the type of the Hits. This may include a special type of "untyped." As stated, this number is typically extended by one, so that sub-strings of the base text 4 can be treated as a "type."

Two annotations with the same type must have different addresses or values. Thus, to distinguish between them, the problem becomes one of ordering the annotations' addresses and values. The addresses refer to a substring (or set of sub-strings) of the base text 4. These implicit sub-strings can be ordered using the two digit (offset, length) scheme as described above. Because two attributes with identical addresses must have different values, and because they are represented as text strings having a lexical order, one additional digit can be used to store the lexical ranking of attributes with identical types and addresses. Thus, three digits can be used to construct a unique number identifying each attribute as shown in the Hits list element 33.

As shown by element 32, four numbers can be used to describe an explicit sub-strings of the base text 4, namely the iref, the htype, the offset and the length. It is noted that the Mark field 27 is used to indicate a context for context-searches, and is described in detail below. Similarly, five numbers can be used to describe any selected annotation 5, as shown by Hits list element 33.

However, typically, the number of annotations in section 5 is much smaller than the length of the base text 4. In this case, the annotations 5 can be ordered with respect to the three-digit scheme as discussed above. In this fashion, only a single number, (the annotation order) is required, and a fourth digit of zero can be used to keep both annotations and base text references in the same numbering scheme. This is depicted in the Hits list element 34.

A stream of Hits 37 can be ordered because of the way it is constructed. Thus, it can be sorted and duplicate Hits can be easily identified and discarded. This property allows a NAT dataset 6 to be searched using multiple terms wherein redundant results can be quickly eliminated. This ordering is also used to great advantage in context searches as described below.

In order to do this all Hits 37 must have another digit of a radix larger than the cardinality of the largest expected Hits stream. This digit holds the number of another Hit in the same Hits stream. For example, consider two Hits "h" and "hc," numbered #h and #hc, respectively. If the Hit h is found in the context of whatever is referenced by Hit hc, the last digit of the number encoding Hit h is #hc. If the last digit of the number encoding any Hit is 0, that Hit was not found as part of a context search. Details of this aspect of context searching are described below.

The format of an Ehit data structure will now be described with reference to FIG. 5. As stated, an E-Hits list 38 is used to display a textual representation of the value referenced in the corresponding Hit. E-Hits, such as Ehit element 35, are used for text processing such as formatting for display. In addition, E-Hits 38 are used for analysis via line oriented text utilities such as grep, awk and sed. Every Ehit, such as Ehit 35, is a single line of text containing 3 or 4 tab separated fields. Any newlines, and/or tabs in the names, types and values referenced by the Hits, such as 32, must be encoded in the corresponding E-Hits, such as 35.

A stream of E-Hits or E-Hits list 38 is thus a stream of text lines. Like a Hits list 37, E-Hits lists 38 are numbered from 1 to the number of E-Hit elements. In a preferred embodiment, there is always a one-to-one correspondence between a stream of Hits list 37 and the E-Hits list 38.

The first field 28 of an E-Hit element 35 is N, the unique name associated with the entry in the NAT dataset 6. The second field 29 is the string representation of the htype digit 25 in the corresponding Hit element (i.e. the name of annotation, or some name that refers to the T section 4). The third field 30 is the value of the selected annotation or the actual base text sub-string. Depending on the intended use of the E-Hits list 38, annotation address information present in the corresponding Hits list may be omitted. However, if the value of a Hit is a sub-string of the base text 4, the offset and length of the sub-string are always provided, although the length can be computed from the sub-string itself.

The fourth field 31 is typically present only if the corresponding Hit element has a non-zero value in its context digit 27. If so, the value of this digit 27 is converted to a text string and becomes the fourth and final field 31 of the Ehit element 35. E-Hits derived from Hits with a zero-value in their context digits 27 have only three fields, such as the Ehit element 36. This fourth field 31 (if present) refers to the line in the E-Hits stream whose number has the value represented by the string in the fourth field.

FIGS. 6A and 6B depict a specific example of an actual entry or "locus" from the Genbank database, which is one example of a NAT dataset 6. In this example, the entry is split into two figures for convenience. It should be understood however, that the actual entry is a single continuous record, in which the information shown in FIG. 6B immediately follows the information shown in FIG. 6A. Accordingly, in the description below, FIGS. 6A and 6B (generally referred to as FIG. 6) are referenced simultaneously.

The actual genetic sequence data 54 is the T (or base text portion 4) of the NAT dataset, and is shown at the bottom of FIG. 6B. As shown, in this example, the genetic sequence data 54 is represented by a string comprising the characters "a", "c", "t" and "g". It should be noted that the genetic sequence data 54 in this example is quite small compared to other typical entries, but is sufficient to describe the features of the present invention. In general, the length of the genetic sequence data 54 is unlimited. For example, the genome for an E-Coli bacterium is approximately 3 million bases long. A "base" is represented by a single character position in the genetic sequence string 54. Accordingly, the genome for this E-Coli bacterium can be represented by a string of characters approximately three million bytes long. Any particular entry in the Genbank database representing a genetic sequence for this organism can comprise a string having any length up to the length of the entire genome.

In this example, the genetic sequence data 54 comprises exactly 293 bases. The numbers 55 listed before each line in the genetic sequence data represent the character position (or the base number) at the beginning of each line. Thus, as shown, line 1 begins with base 1, line 2 begins with base 61, line 3 begins with base 121, and so on. As shown, the sequence data 54 is divided into groups of 10 to facilitate base number identification for human investigators.

Although the entry shown in FIG. 6 is quite small, it displays nearly all the elements of the flat file format used by Genbank. It is important to note that the Genbank flat file format is just one example of NAT dataset that can be used in conjunction with one embodiment of the present invention. In the examples below, the Genbank flat file is used to distinctly point out and describe the details of a preferred embodiment of the present invention. Persons skilled in the relevant art(s) would appreciate that the present invention can be used with any type of database or file format. Accordingly, by reading the present disclosure, persons skilled in the relevant art(s) would be able to apply the principals presented in the examples herein to other databases and file formats for the purpose of implementing alternate embodiments of the present invention. As such, the Genbank examples presented herein should not be construed to limit the scope and breadth of the present invention.

In addition, the meaning and use of the various fields and data elements listed in the Genbank data entry shown in FIG. 6 is well known by persons skilled in the relevant art(s). Accordingly, the meanings of the data fields are not fully described in herein.

The unique element name 2 in this example entry is shown in the LOCUS section. Specifically, in this example, the unique name is "ANANIFDR2. " The portion of the Genbank entry above the genetic sequence data 54 is referred to as the annotation portion 5, as described above. The annotation portion in this example is organized into several sections. Each section of the annotation is introduced by a keyword located in column one as shown in FIG. 6A. In this example, the sections are as follows: LOCUS 40, DEFINITION 41, ACCESSION 42, NID 43, VERSION 44, KEYWORDS 45, SEGMENT 46, SOURCE 47, REFERENCE (1) 48, REFERENCE (2) 49, COMMENT 50, FEATURES 51, BASE COUNT 52 and ORIGIN 53. The final section is the base text section and is referenced in this example as 54. These annotations are each typically assigned a htype value, as described above.

Some of the sections described above comprise one or more subsections. For example, ORGANISM 60 is a subsection of SOURCE 47. Similarly, the REFERENCE SECTIONS 48 and 49 have various subsections as follows: AUTHORS 61 and 63; JOURNAL 62 and 65; TITLE 64; and MEDLINE 66. The FEATURES section 51 comprises two subsections: source 67 and CDS 68.

It should be noted that any of the annotations could reference sub-strings of the sequence data 54. For example, the FEATURES section 51 contains pointers or addresses of actual sequence data listed in the sequence section 54. The sequence data 54 is referenced according their base numbers or character positions. A description of base number addressing schemed used by Genbank is described in detail below.

The REFERENCE section is the only annotation type in this example that can appear more than once in accordance with Genbank data file standards. In this example, two REFERENCE sections 48 and 49 are used. All of the other sections shown in FIG. 6 are required sections according to Genbank data file standards.

As shown, the subsections are introduced by a keyword that is slightly indented from their associated sections. The amount of indentation varies depending on the particular section. For example, the subsections of the FEATURE section 51, namely, the source 47 and CDS 48 subsections, begin in column six. The subsections of the REFERECE sections 41 and 43 and the SOURCE section 47 begin in column 3.

In general, this type of data formatting information is necessary for parsing the NAT database 6 in accordance with an embodiment of the present invention. Parsing in this manner is well know in the art and therefore not discussed in detail herein, other than pointing out the particular parsing considerations using the Genbank database as an example. The specific data parsing requirements that should be implemented in any particular embodiment of the present invention, for creating the Index and PSKEL files (described below), depend on the actual NAT dataset being used. Specific methods for parsing such datasets would be apparent to persons skilled in the relevant art(s), after reading the examples presented herein.

In this example, all sections use one of three basic formats as described below. A first type of formatting is used for all sections except the FEATURES 51 and the genetic sequence sections 54. A second type of formatting is used for the FEATURES 51 section and a third is used for the genetic sequence information 54.

Format 1 is used for all sections except FEATURES 51 and the sequence information 54. Each Format 1 section is introduced with a line that begins with the section keyword in column one. For example, the LOCUS section 40 begins with the keyword "LOCUS" in column one. Data for the section immediately follows this keyword beginning in column 12, and continuing up to column 79, as shown in FIG. 6A.

If the data does not fit on a single line, it is continued onto one or more lines that immediately follow the first line of the section. For example, the DEFINITION section 41 continues with the word "end.", on a continuation line immediately following the section line 41. As shown, data in continuation lines also begin in column 12 and continues up to column 79 if necessary.

The interpretation of the leading spaces on the continuation lines depends on the section. Generally the data in a section can be considered to be a single (possibly very long) line, meaning that the leading spaces on each continuation lines can be collapsed into a single space. There is, however, one exception to this general rule. The SOURCE section 47 contains one required subsection, namely ORGANISM 40, which always contains at least two lines. The first line 40 contains the name of the organism, usually as a genus species pair. This is sometimes followed by additional information.

The second line 47 and subsequent lines (if required), are indented in a similar fashion as continuation lines. However, in this case, they are not continuation lines but are actually an unmarked subsection (i.e. a subsection without a keyword). These lines contain the source's complete phylogenetic information and while they themselves behave as a single long line, they are not a continuation of the ORGANISM line 40.

This format is also used for the REFERENCE sections 48 and 49. Each REFERENCE section 48 and 49 can have up to five subsections from the set of: AUTHORS, TITLE, JOURNAL, MEDLINE and REMARK. Of the five subsections, only the AUTHORS 61 and 63 and JOURNAL 62 and 65 are required subsections of the REFERENCE section 48 and 49. Instances of all subsections except REMARK are shown in FIG. 6A.

In addition to the usual bibliographic information found in scientific citations, the first line of each REFERENCE section 48 and 49 typically contains a list of exactly which bases in the sequence are associated with the work described in the reference. Thus, for example, the REFERENCE section 48 refers to bases 1 to 10 and 277 to 293, as shown.

The second basic section format is used for the FEATURES section 69. The FEATURES section 69 is generally considered to be the most complicated part of the Genbank flat file. The FEATURES section 69, sometimes referred to as the "feature table," is used to annotate or describe the sequence 54, or at least those regions of the sequence 54 about which something is known. The feature table 69 is used to identify functional or interesting subsequences including, but not limited to, protein coding regions, introns, promoters, mutation sites and regions of genetic variability. The mechanism used is quite extensible and provides a general way to attach information about a part of the sequence to that part of the sequence.

The feature table 69 consists of a two level hierarchy of annotations or features, each consisting of a feature name, the address of the bases involved, and zero or more qualifiers that provide a detailed description of the feature. The address is actually an expression that can be used to describe essentially any substring of the bases in Genbank, including bases in other entries. The qualifiers, which explain why these bases are interesting, consist of a short word beginning with a slash (/) possibly followed by an equal sign (=) followed by the qualifier's value.

As shown, feature names begin in column six and are immediately followed by the address of the bases involved, beginning in column 22 of the same line. If the address is too long to fit on a single line, it is continued on subsequent lines, where each continuation line begins with 21 leading spaces. If an address spans several lines, the leading spaces on its continuation lines are discarded when computing the address. All qualifiers begin on a new line in column 22 following 21 leading spaces and may also span several lines. Like address continuation lines, qualifier continuation lines begin with 21 leading spaces, but unlike address continue lines, the significance of the leading spaces depends on the qualifier. Because a qualifier begins with a slash, and no slashes are involved in base addressing, the boundary between the end of the address and the first qualifier is unambiguous.

Unfortunately, determining the boundary between qualifiers is somewhat more difficult because the contents of a continued string valued qualifier (discussed below), can look identical to the beginning of the next qualifier. This case is preferably resolved by maintaining a context of the current qualifier, but it is another of the things that makes working with the flat file format so tricky. Finally, the end of a feature's qualifier list is reached when a new feature is encountered (indicated by a word in column six) or the next section (BASE COUNT 52) is reached.

Every qualifier has a type and accepts values of only that type. There are several types of qualifier values: Boolean, integer, citation, keyword, string and compound. Of these types, only Boolean qualifiers have no explicit values. This is because the Boolean values are true or false depending on their presence or absence in the qualifier list. That is, a Boolean value is true if it is present in the feature's qualifier list. Similarly, a false value is indicated by the qualifier's absence in the feature's qualifier list.

All other types of qualifiers require an explicit value, which is separated from the qualifier's name by an equal sign (=). No spaces are permitted around the equal sign. An integer value is a string of decimal digits, e.g., 23. A citation value is an integer surrounded by square brackets and it refers to a REFERENCE section, such as 41 in the entry. For example, "[2]"is a citation value and it refers to the second REFERENCE section 43 of the entry. A keyword value is a sequence of letters, e.g., left, right or their upper case variants.

A string value is any sequence of characters that begins and ends with a double quote ("). Due to the fixed format nature of the flat file, the end of the string is unambiguous and internal double quotes need not be escaped. However, since a string can contain any sequence of characters and may continue over several lines, any program that reads the flat file format must distinguish between a qualifier name and a string containing a qualifier name that just happens to begin a qualifier continue line.

Compound values are enclosed in parentheses and contain a "rule". A rule is a comma (,) separated list of conditions, where a condition is two non-blank entities (keywords, strings, etc) separated by a colon (:). The allowed symbols and their meaning are dependent on the qualifier. For example, the /codon qualifier takes a rule value as shown below:

/codon=(seq:"tga", aa:Trp)

This qualifier indicates that for the scope of this feature (a single coding sequence), the base triplet gac is a tryptophan codon instead of the usual stop codon.

The third and final format used in the Genbank flat file is used to hold the actual sequence information in section 54. This is the only section without an introductory keyword and is the last section of each Genbank entry or locus. The sequence 54 is listed as lines of lower case letters. The letters are always "a," "c," "g" and "t". A lower case n is used to indicate an unknown base. Each line of sequence begins with the base number 55 of the first base of that line and contains up to 60 bases separated into groups of ten (except for possibly the last group of the last sequence line), by a single space.

Base numbering begins at one. All bases including long runs of n's must be listed even though each line's initial base number would allow such runs to be implied by a jump in these numbers. Because only five types of bases (including unknown) are supported in the format, non-standard bases must be indicated in the feature table.

Two types of base addressing are used to link information in the annotation section of the entry to specific bases in the sequence section 54. A simple range list system is used in the REFERENCE sections 41 and 43, while much more powerful string expressions are used in the features table 69.

There are two forms of range lists, those covering bases and those covering sites. Both bases and sites forms begin on the REFERENCE line in column 12. The sites form of range list consists solely of the string "sites."

The bases range list, as shown in 41 and 43 begins with the string "bases," followed by a semicolon to separate range lists, and ending with a right parenthesis. This style of addressing can span several lines, where continue lines are indicated with 12 leading spaces. A range is simply two integers representing the beginning and end base number, separated by the keyword "to." The leading spaces on range continue lines are discarded when computing the address. Both REFERENCE sections 41 and 43 in this example use base format addressing.

Range lists are not powerful enough to describe the all of the things that genetic sequences can code for, and therefore, must be representable in the feature table 69. Features use address expressions to specify the bases they describe. Address expressions consist of integers, labels, several infix and prefix operators and a number of functions that provide several ways to combine or modify their argument strings.

The bases in the sequence are listed beginning with the "5' end" (see DEFINITION 41) and are numbered left to right from 1 to N, where N is the total number of bases in the sequence; an integer, i, in an address expression refers to the $i^{th}$ base of the sequence. An integer may be preceded by one of the prefix operators <and > which indicate that the address may actually begin before or continue after the specified base. Prefix operators are used in partial sequences where the true beginning and/or ending of the feature lies outside the beginning and/or of the physical sequence reported in the entry. They are also used to indicate uncertainty as to the boundaries of a feature.

A double dot (..) or a caret may separate two (possibly prefixed) integers (A). A double dot indicates the sub-string of bases from the first to the second integer including the end points. The caret symbol indicates the position between the two integers. Two integers enclosed in parentheses separated by a single dot (.) denotes any single base in the inclusive range. Any of these constructs: integer, string, insertion point or range may be preceded by a label separated from the construct by a colon (:) to indicate that the construct is not from the current entry, but from the entry whose accession number and version match the label.

Five functions are provided to operate on string valued constructs and all five return one or more strings. The functions are complement, group, join, one-of and order. A function invocation begins with the function name followed by its argument(s) enclosed in parentheses. The function complement takes a single argument while the other four take two or more. Multiple arguments are separated by a comma (,). The function one-of returns a set of strings as discussed in the table below.

TABLE 1

| Function | #Args | Action |
| --- | --- | --- |
| | Genbank Address Functions | |
| complement | 1 | Return the Watson/Crick complement of the input string. |
| group | ≧2 | The sequences in the input are to be kept together, but nothing is known about their order or if they are contiguous. |
| join | ≧2 | The sequences in the input are to be kept together, but nothing is known about their order or if they are contiguous. |
| one-of | ≧2 | Choose one of the strings in the argument list when the address expression is evaluated. Any address expression containing a one-of( ) call generates a set of sequences, one sequence for each argument in the one-of( ) call. If an expression contains more than one one-of call, the number of sequences generated grows as the product of the size of their argument lists. |
| order | ≧2 | The sequences specified by the argument are to be kept together in the order specified list; however, no claim is made that they are contiguous. |

The operations defined by these functions support rather arbitrary expressions with any level of nested calls. However, a combination of a canonical form and the fact that these expressions represent genetic sequence processing, imposes some restrictions on the expressions that can be seen. To date, all such genetic processing has consisted of assembling discontinuous subsequences from one strand of the sequence into a longer almost always contiguous sequence.

In some cases, choices may exist as to which pieces are assembled. All such sequences can be constructed from a single join( ), order( ) or group( ) call containing a mixture of literal subsequences and/or one-of( ) calls, which themselves contain literal subsequences. Finally should the actual sequence be on the other strand, the whole expression is passed to complement( ). This means that an expression contains at most one complement( ) call and it is always the outermost or top level call.

Figure 7:
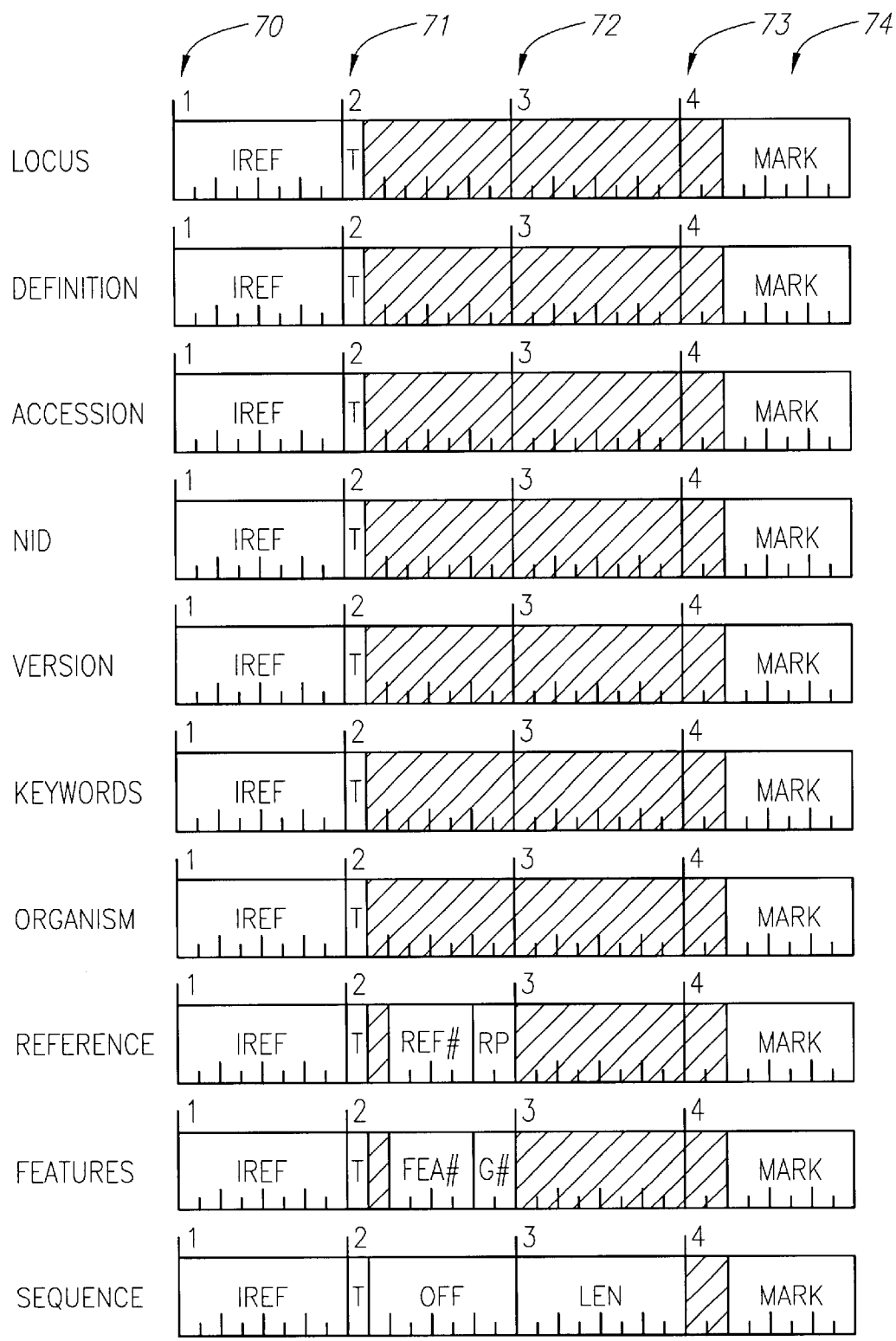
FIG. 7 is a block diagram depicting a data format of a Hits list that can be used with the file format of the Genbank database, in accordance with an embodiment of the present invention.

FIG. 7 is a block diagram depicting a data format of a Hits list that can be used with the file format of the Genbank database as described above. The example shown in FIG. 7 is a specific instance of a Hits list format as described above with reference to FIG. 5.

Referring now to FIG. 7, the Hits list comprises 4 digits 70, 71, 72 and 73. As shown, the mark indicator 74 is imbedded in the forth digit 73 to indicate a context search. In this example, the iref number 70 is 32 bits wide (each tick mark represents 4 bits). Thus, this embodiment can hold up to $2^{32}$ entries or loci.

Next, as shown, the htype field 71 is 4 bits wide. Thus, up to $2^4$ or 16 types can be identified (including the base type and untyped, if available). In this example, there are no untyped data types. It should be noted that remaining 28 bits in the second digit 71 are not used except for REFERENCE, FEATURES and SEQUENCE types. As shown, in this example, REFERENCE types use two additional numbers to describe the Hit. Specifically, 16 additional bits are used to store the reference number and 8 additional bits are used to store the reference part.

Similarly, FEATURES types use two additional numbers to describe the Hit. Specifically, 16 bits are used to store the feature number and 8 bits are used to store the qualifier number. In addition, a type of SEQUENCE (which refers to the base text section 4) uses two additional numbers to describe the sub-string. Specifically, 28 bits are used to store the offset and 32 bits are used to store the length.

A preferred embodiment of the present invention can be implemented using an interactive graphical user interface for specifying and refining database queries. One example of such an interface is provided by the "AVS™" visual application development environment manufactured by Advanced Visual System, Inc., of Waltham Mass. Another example of a visual programming development environment is the IBM® Data Explorer, manufactured by International Business Machines, Inc. of Armonk, N.Y.

It is noted that using a visual-programming environment, such as AVS, is just one example of a means for implementing a preferred embodiment of the present invention. Many other programming environments can be used to implement alternate embodiments of the present invention, including customized code using any computer language available. Accordingly, the use of the AVS programming environment should not be construed to limit the scope and breadth of the present invention.

In this example, the AVS system is used to implement a preferred embodiment of the present invention for a number of reasons. Using such a system reduces custom programming requirements and speeds up development cycles. In addition, the visual programming tools provided by the AVS system facilitate the formulation of database queries by researchers who are not necessarily knowledgeable about databases and programming languages. In addition, an advantage to using a programming environment such as AVS, is that the system automatically manages the flow of data, module execution, and any temporary data file and storage requirements that may be necessary to implement requested database queries.

AVS is particularly useful because it provides a user interface that is easy to use. To perform a database query, users construct a "network" by interacting with and connecting graphical representations of execution modules. Execution modules are either provided by AVS or are custom modules that are constructed by skilled computer programmers. In the examples below, much of the present invention is implemented with the use of customized AVS modules constructed using a high level programming language, such as C, C++ or FORTRAN, in accordance with the principles described below.

The purpose of constructing a network in AVS is to provide a data processing pipeline in which the output of one module becomes the input of another. Using the present invention, database queries are formulated in this manner. A component of the AVS system referred to as the "Flow Executive" automatically manages the execution timing of the modules. The Flow Executive supervises data flow between modules and keeps track of where data is to be sent. Modules are executed only when all of the required input values have been computed.

Figure 8:
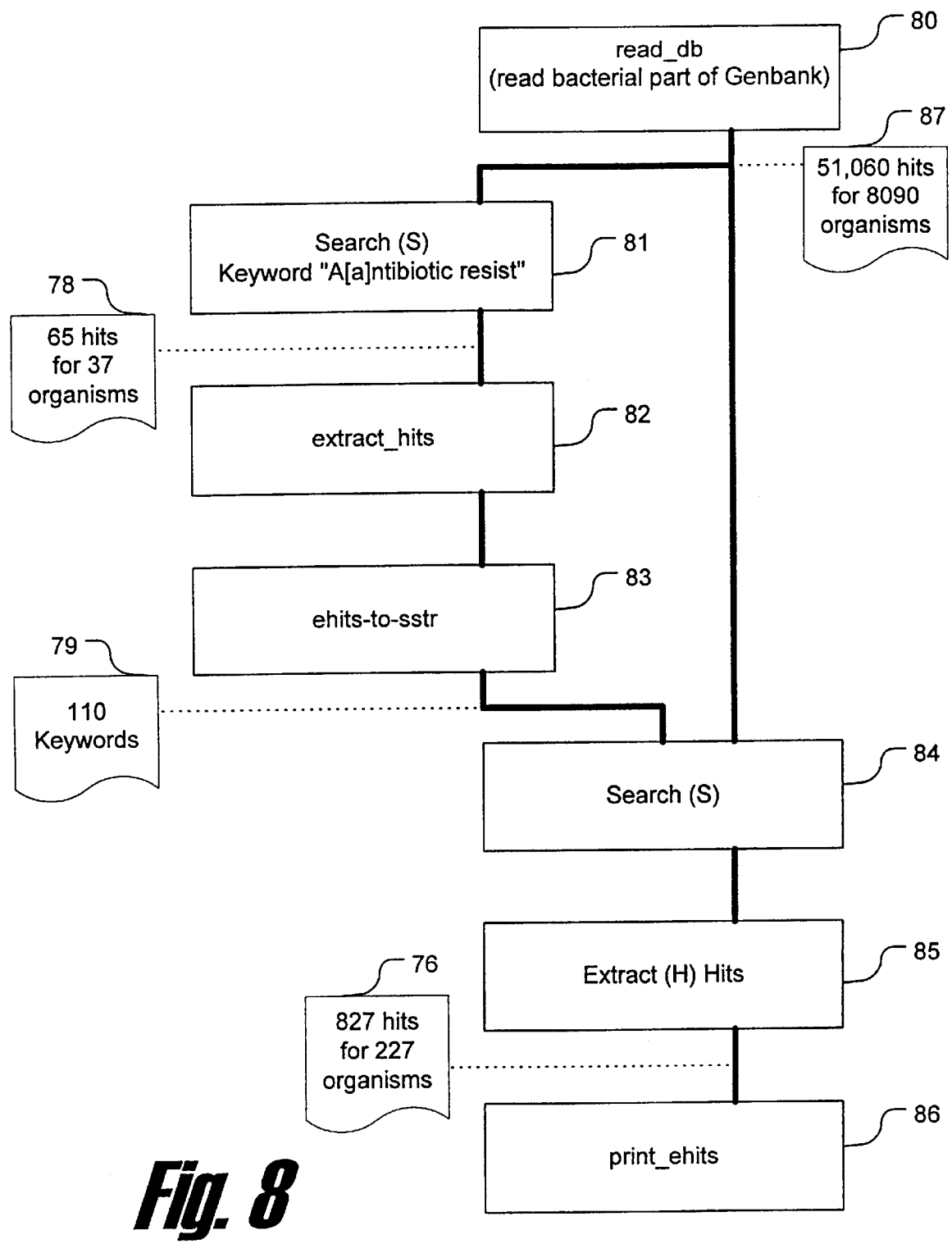
FIG. 8 is a block diagram depicting a computational network that implements a search in accordance with a data mining embodiment of the present invention.

FIG. 8 is a block diagram that is useful for describing the network feature of the present invention using the AVS or similar programming environment. In addition, FIG. 8 depicts an example of an actual database query that can be formulated and performed in accordance with the principals of the present invention. In particular, this example depicts the use of an interactive database query in accordance with a preferred embodiment of the present invention.

As stated, the complexity of genetic sequence data makes it difficult, if not impossible, to formulate a single database query that will return an acceptable set of relevant results. This is due to a number of factors, including an imprecise understanding of the relationships between sequences and functions, as well as the lack of a standard vocabulary for annotating even well understood sequences.

The former results in sequences that are at best partially annotated, but more often contain incorrect annotations or annotations that, while true, are so trivial that they are not really useful. The latter factor results in a multiplicity of ways to describe the same object, or type of objects, and, as most of these ways are not obvious, they can be discovered by examining the search results.

Accordingly, from these considerations, the present invention provides an interactive search style, where an informed user can examine the results of a search stage. The results are then "edited" and used as new keywords for performing one or more subsequent searches. This process can be repeated as often as necessary to obtain a desired result resolution. Typically, this involves removing unwanted Hits and/or combining results of related searches, some of which use new search keys extracted or derived from an earlier search.

Referring now to FIG. 8, a network for formulating a database query is shown. The network comprises a number of custom modules that each performs a specific function. The top portion of each module represents the input(s) and the bottom portion represents the output(s). All of the inputs and outputs in these examples are defined as vectors. That is, the inputs are preferably designed to operate on a list of data items just as easily as a single data item As stated, AVS and other visual programming network environments function such that a module is not executed until the input data (generally the output from an execution module), is available. Thus, for example, the search database function 81 is not executed until the read database function 70 has completed.

In this example, the first operation that is performed is the read database function 80. In general, the output from a read database function is a specified portion of the Genbank database formatted as a Hits list 37. Typically, the user specifies parameters by selecting one or more entries from a list comprising the various database sections. In this example, it is assumed that the bacterial portion of the Genbank database is selected. As indicated, the output 87 from this function 80 results in 51,060 entries for 8,090 organisms.

The means by which the user specifies input parameters associated with modules depends on the particular module and on each specific implementation of the present invention. In this example, using AVS, a pre-defined control panel is automatically displayed a particular module is selected. The control panel can also be displayed via a control panel push button. The user interacts with the control panel to enter relevant parameters associated with the module. In this example, the user simply selects the Bacterial portion of the Genbank database from the list presented in the control panel.

Next, as indicated, the search (S) database module 81 is executed with the Bacterial section of the Genbank database 87 as the input parameter. All of the modules that are labeled as "Search (S)", perform the function of the Search (S) module 10, as described above. Similarly, the modules labeled Extract (E) Hits, such as module 85 perform the same function as the Extract (E) module 22, as described above. An example of the Context Search (CS) module 14 is described below with reference to FIG. 9.

Continuing with the description of FIG. 8, the user is prompted to enter one or more search parameters or search keys 9, to be used by the Search (S) module 81. These parameters include keywords, Boolean operators and other parameters generally associated with database search queries in accordance with each specific implementation of the present invention. In this example, the user enters the keyword "[Aa]ntiboitic resist". This causes the search database module 81 to search the Bacterial section for the specified keyword. The result in this example is a Hits list 88 representing 65 entries from 37 different organisms.

At this point in the process, the researcher analyzes the results 88 (via the Extract module 82), and reasons that the number of entries is too small. This discrepancy is due to the lack of a standard vocabulary used for annotating the database as described above. The researcher suspects that there are many more entries in the Bacterial portion of Genbank that are characterized as being resistant to antibiotics. However, these additional entries were not found because they were described using different keyword descriptions.

However, visual or electronic inspection of the search results 88 reveals many of the different descriptions to the investigator. Accordingly, the extract hits module 82 is used to present these results to the user. In this fashion, one or more keywords can be manually or automatically selected.

The output from the extract hits module 82 is fed into the input of the extracted hits (E-Hits) to string module 83. The E-Hits to string module 83 simply processes the extracted hits into a new set of search strings that are used as input parameters for the second execution of the search database module 84. Thus, all of the extracted keywords, such as "penicillin resist" and "beta-lactamase" (taken from the 65 hits in the Hits list 88) are converted into a new set of search strings. In this example, the output 79 of the E-Hits to string module represents 110 keywords, including the original keyword "[An]tibiotic resist."

Next, as indicated, the search database module 84 is again executed with two inputs. The first input is Hits list 87 representing the Bacterial database portion from the read database module 76. The second input is the set of search strings from the E-Hits to string module 83 that is used as keywords to perform the second database search. The output 76 of the search database module 84 is a Hits list that represents 827 loci covering 227 different organisms. This represents a 13-fold increase from the original search.

Figure 9:
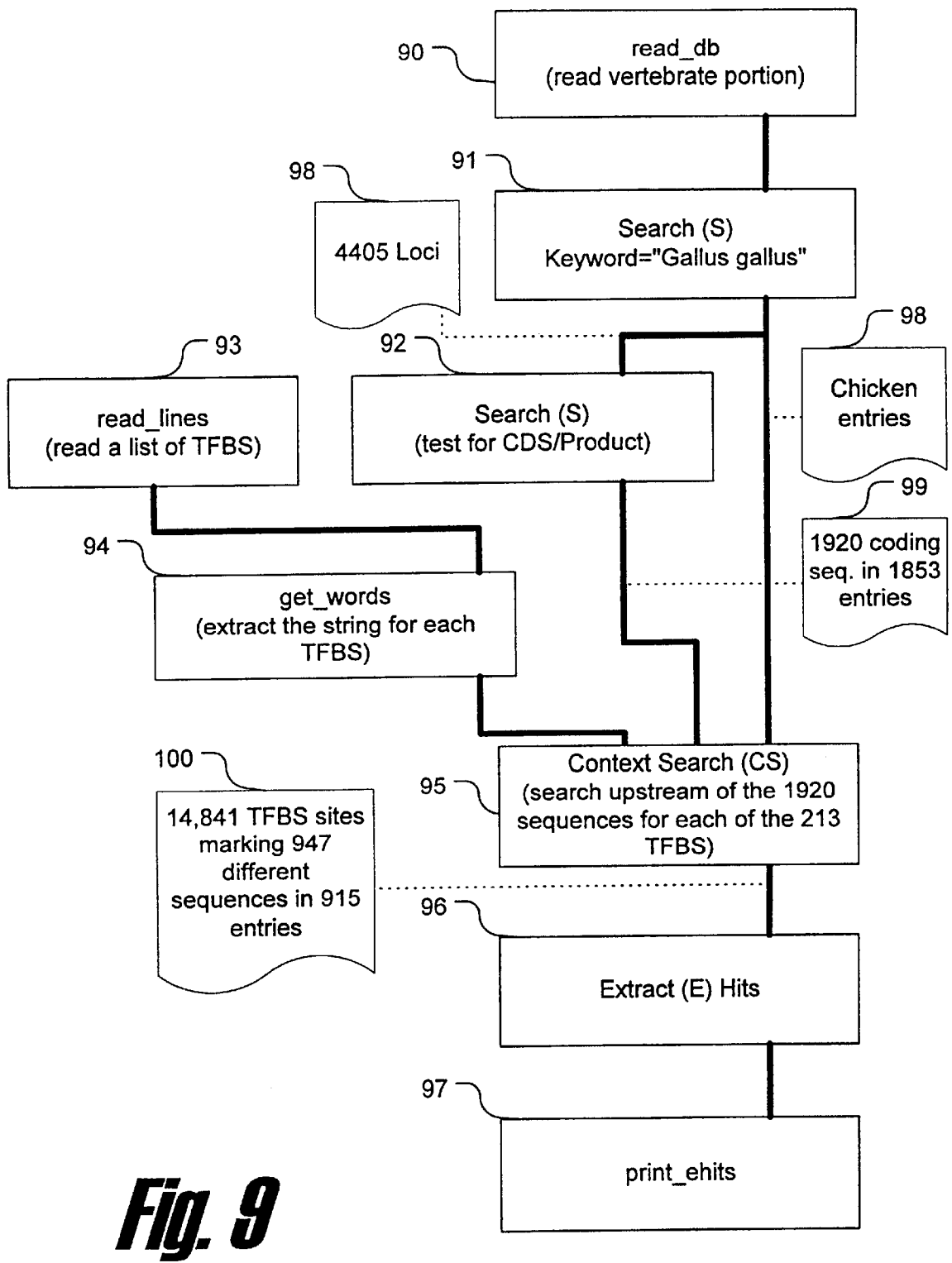
FIG. 9 is a block diagram depicting a computational network that implements a context search in accordance with an embodiment of the present invention.

FIG. 9 is a block diagram depicting another network that can be used to perform a context search in accordance with a preferred embodiment of the present invention. Before describing this example, the concept of a context search and its importance to researchers using the example of genetic sequence data, is described below with reference to the sequence shown in FIG. 6B.

Consider a search for instances of the sequence "ttt." This example shows how the value of sequence information is increased by being able to use data associated with that sequence. This sequence occurs eight times in the sequence data entry 54. Four of these instances occur in the two tttt tetramers. Specifically, the instances begin at base numbers 3, 4, 22, 108, 124, 125, 152 and 284.

The meaning of the sequence depends on its position and from the feature table 69. It can be seen that six of the eight entries (those in positions 3, 4, 23, 108, 124 and 125) are in a protein coding sequence, It can also be seen that no additional information is available about the last two sequences beginning in positions 152 and 284. The feature table 69 further explains that the coding sequence is actually on the other strand, which is complementary to the one in the entry.

The protein (actually a peptide) begins in position 128 and continues right to left to position 1 and beyond as indicated by the prefix <before the 1 in the feature's address (see line 48). Translating the sequence into amino acids shows that only the two tt's (at positions 3 and 108) are in phase and represent (via their complements, aaa) the amino acid lysine while the other four tt's are out of phase and do not have any meaning by themselves, being split between two consecutive codons.

The second example is the inverse of example above. This time the search is for information about a peptide whose name is "xisA peptide A." Such a search would return (at least) the entry in FIG. 6, which contains this string as part of the value of a /note qualifier attached to a CDS (Coding Sequence) feature 48. Although the amino acid sequence of this peptide is provided as the value of a /translation qualifier, due to the redundancy of the genetic code, the original nucleotide sequence is ambiguous. However, if the feature is completely identified, the feature's address expression can be applied to the entry's sequence yielding the associated sequence.

The sequence search in the previous example shows why context searching is important. The eight "ttt" sequences found in that entry has three meanings: a lysine codon complement, parts of two consecutive codons' complements and unknown" depending on where the "ttt" is located in the sequence data 54. Although this example was selected both for its simplicity and the fact that the returned strings have multiple meanings, one or more of the same three meanings would have applied to any sequence found in this Genbank entry depending on its location. For this reason, it is extremely useful to be able to specify the context for a search, so that only those instances of the search string that have a particular meaning are returned.

In this example, the search for "ttt" suggests at least four possible contexts: 1) in a protein/in-phase, 2) in a protein/out-of-phase, 3) in a protein and 4) unspecified. However, this is just beginning of the useful context relations. Below are some additional examples. Transcription factor binding sites and promoters are short nucleic acid sequences that are upstream of a coding sequence. Attenuators are short nucleic acid sequences that can fold up into specific stem/loop structures are downstream of a coding sequence. Restriction sites required for specific genetic manipulation may need to be "upstream," "downstream" or "within" the target site. Thus, what is needed is a general way of searching for any "functional entity" (defined below) in any context of any other functional entity.

A functional entity is defined herein as a set of bases (or character positions) that for some reason should be treated as a single object. They might for example, code for a protein, be a restriction site, or be capable of assuming a specific RNA secondary structure. The actual function is not important. What is important is that these bases be treated as a single object. Functional entities include all non-empty subsequences (the actual sequence reported in the entry), as well as implied subsequences.

Implied sequences are created by applying the address expressions attached to the annotations (from the FEATURES section 51 and/or REFERENCE section 41 and 43), to the actual sequence data. Thus a general context search algorithm preferably supports any of the following four types of context searches:

TABLE 2

Context Searching

| Search For | In Context Of |
| --- | --- |
| Sequence | Sequence |
| Sequence | Annotation |
| Annotation | Sequence |
| Annotation | Annotation |

An example of a query that illustrates a context search is shown in FIG. 9. In this example, consider transcription factor binding sites (TFBS). These are short sequences (i.e.

5–10 bases) that when located upstream (5') of coding sequences, affect transcription of the gene. If TFBS are located anywhere else, they may have other functions. Thus, a simple search of TFBS sequences is not sufficient because most of the hits will not be true transcription binding sites, but rather irrelevant matches of the TFBS sequence. Further there is no way to determine which of the results are true TFBS hits.

The solution to this problem is to perform a search in context of coding sequences. First, a search is performed to find all coding sequences. These hits are used to "mark" regions that are downstream of the coding sequences. The marked regions are used as the context in which to perform a second search. The second search is performed only on the marked regions and the TBFS sequences therein are extracted. This returns only true TFBS hits. An example of this method is described below with reference to FIG. 9.

In FIG. 9, a search is performed in the Vertebrate database to search for TFBS for chickens. As shown, the first step is to execute the read database module 90. The output (not shown) is the vertebrate portion of the Genbank database. Next, as indicated, the search database module 91 is executed. In this case, the user enters search parameters to extract all "Gallus gallus" (chicken) entries from the database. As indicated by the output block 98, this results in a total of 4,405 entries.

Next, the search database module 92 is again executed. This time the input is the 4405 chicken loci from module 81. This time the search is performed to find coding sequences (CDS). A read lines module 93 is executed in parallel for reading in a pre-compiled list of named TFBS sequences. Next, as indicated, a get-words module is used to extract the sequence from each of the named TFBS sequences.

Next, the search database module 95 is executed. The search database module 95 has three input parameters. The first input parameter is the Hits list 98 comprising the 4405 chicken loci. The second parameter is the Hits list 99 comprising the 1920 coding sequences. The coding sequences 99 are used to provide a context to the context Search module 95. This context is used in conjunction with input parameters from the user that defines the relationship for the context. For example, the user can specify a search for TFBS sequence strings 93 that are within 500 bases upstream of the coding sequences 99. Details of the data structures that can be used to implement this context search are described below, with reference to FIGS. 15–18.

Figure 10:
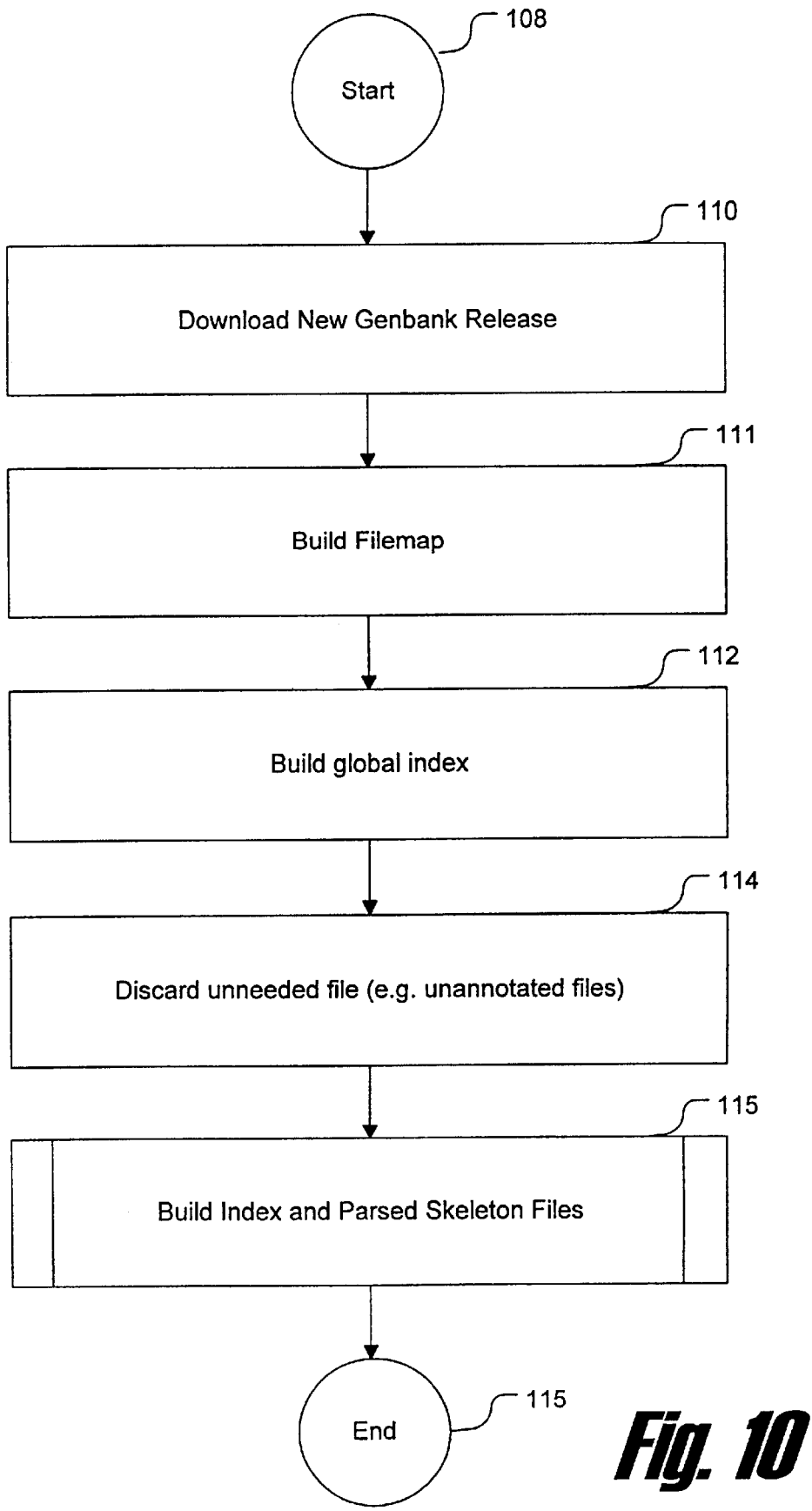
FIGS. 10 and 11 are flowcharts depicting processes that can be used to implement the present invention.

FIG. 10 is a flowchart depicting a process that can be used to implement the present invention. The process begins with step 108, where control immediately passes to step 110. In step 110, the Genbank release is obtained. Generally, this occurs by downloading a number of files from the NCBI Website, as described above. Currently, the Genbank release comprises about forty-five flat files.

Next, in step 111, a file map is constructed. The file map is used to determine where a particular locus is located. That is, which one of the 45 files downloaded in step 110 contains a particular locus. A detailed example of the contents of a file map is described below with reference to FIG. 12.

Next, in step 112, a global index is constructed. In this example, the global index comprises the names of all of the loci contained in the Genbank release (i.e. in all 45 files) along with a unique identifier (ID) for each locus. This file is typically sorted in the order of the locus names. A detailed example of the contents of a global index is described below with reference to FIG. 12.

Next, in step 114, the user typically discards any Genbank files that are not needed. For example, a user may discard all of the unannotated sequence files. Next, in step 115, the process builds an index and parsed skeleton files (PSKEL) for each of the Genbank sequence files. A detailed example that describes the contents of the index and the PSKEL files are described below with reference to FIG. 13.

Figure 11:
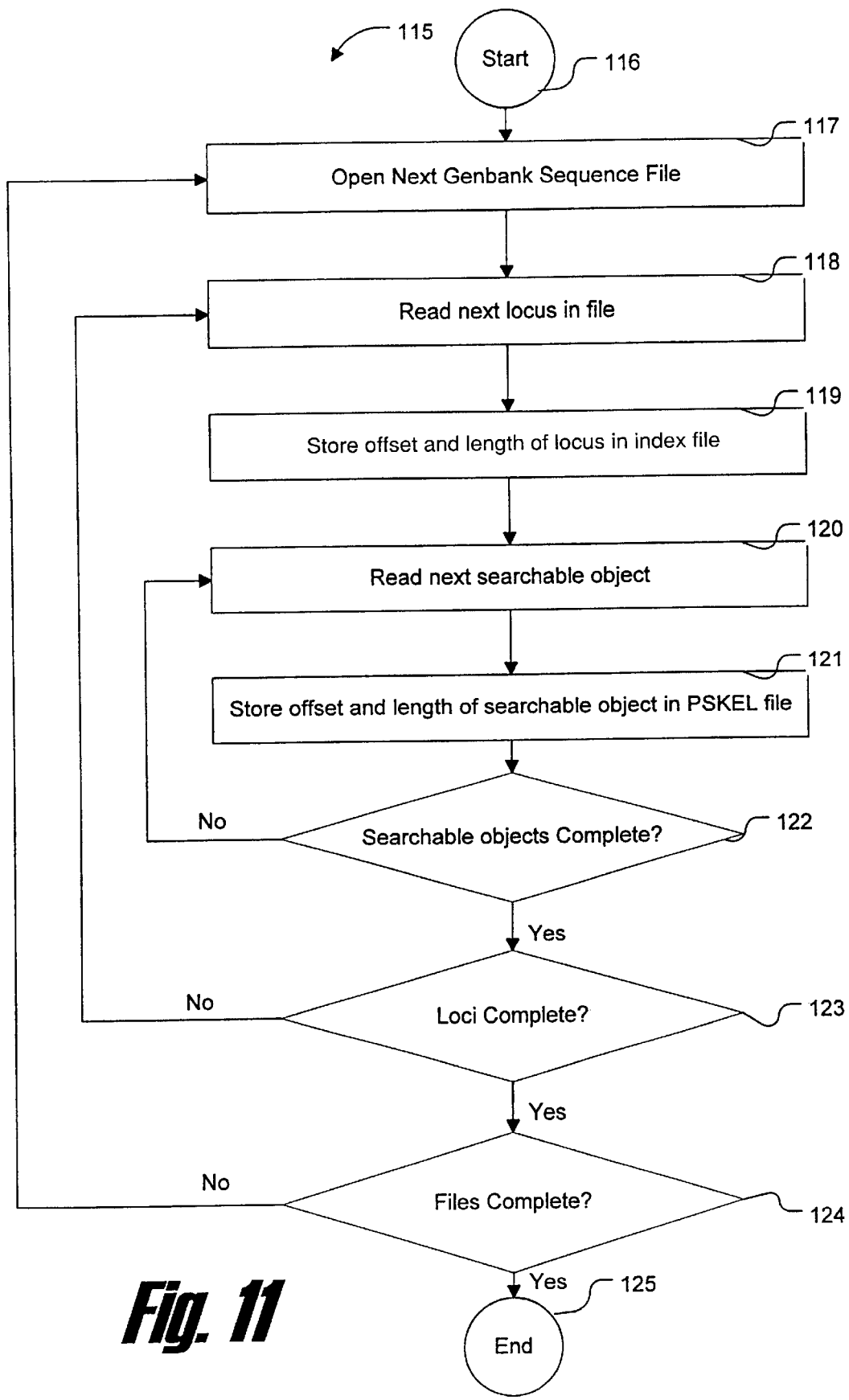

FIG. 11 is a flowchart that depicts a process that can be used to implement step 115 for building the index and PSKEL files for each Genbank sequence file. The process begins with step 116, where control immediately passes to step 117. In step 117, the process opens the next Genbank Sequence file. Typically, the Genbank sequence files are opened in the order they appear in the file map, as described below. Thus, the first time step 117 is executed, the first file listed in the file map is opened.

Next, in step 118, the process parses the file and reads the next locus in the file. Of course, the first time step 118 is executed for each Genbank file, the first locus in the file is read. Next, as indicated by step 119, the offset and length of the locus read and parsed in step 119 is stored in the index file associated with the Genbank sequence file. Typically, the index file has the file same name (but different file type), as the associated sequence file for identification purposes. For example, for a bacterial file named "BCTI.SEQ," the associated index file is named "BCT1.INDEX."

Next, as indicated by step 120, the next searchable object is read. For example, the first time this step is executed, the LOCUS section is read and its offset and length are determined. This offset and length is next stored in the associated PSKEL file, as indicated by step 121. Typically, the PSKEL file has the file same name (but different file type), as the associated sequence file for identification purposes. For example, for a bacterial file named "BCT1.SEQ," the associated PSKEL file is named "BCT1.PSKEL."

Next, as indicated by step 122, the process determines if there are additional searchable objects in the locus. If so, control loops back and steps 120 and 121 are executed, thereby storing offsets and lengths for all searchable objects in the locus, until all searchable objects have been processed. The last searchable object in each locus is the sequence data 54, as shown in FIG. 6B.

As indicated by step 122, once all searchable objects have been processed, control passes to step 123. In step 123, the process determines if there are any additional loci remaining in the file read in step 117. If so, control passes back to step 118, and the next locus is processed in the same manner as described above. Once the last locus in the file has been processed, control passes to step 124, as indicated.

In step 124, the process determines if there are any more files listed in the file map that need to be processed. If so, control passes back to step 117, where the next Genbank sequence file is opened. Next, the process repeats itself, as described above, until all Genbank sequence files have been processed in the manner described above. Finally, as indicated the process ends with step 125.

Figure 12:
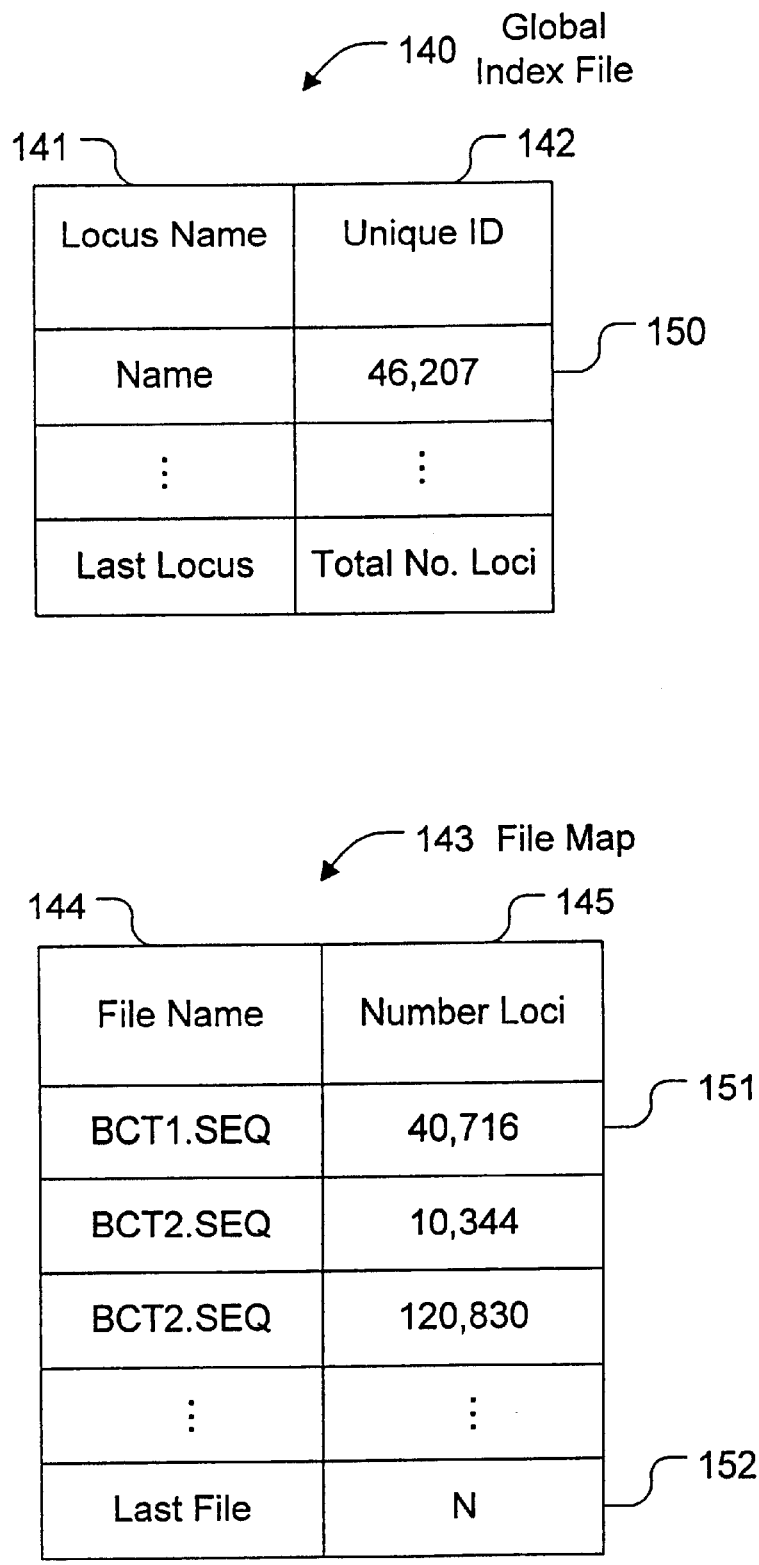

The net result of the process depicted in FIG. 11, are the creation of an index file and a PSKEL file for each Genbank sequence file used in a particular implementation of the present invention. FIG. 12 is a block diagram depicting the contents of a global index file and a file map in accordance with a preferred embodiment of the present invention.

As shown, the global index file 140 comprises the unique name 1 of each element in the NAT database 6 (in this example, the Genbank database), and a unique ID 142 that is assigned to each element. Typically, the unique ID 142 assigned is simply the order number in which the entry appears in the Genbank database. Typically, when multiple files are used, their ordering is performed in according to the file map described below.

The file map 143 in this example comprises the file name of each file in the Genbank database, and the number of entries (loci) within each file. Thus, given a loci number (i.e. the unique ID 142 assigned to each loci, as described above), one can easily determine which file contains the entry by consulting the file map 143.

FIG. 13 is a block diagram depicting the contents of the index file 160 and the PSKEL file 170 in accordance with an embodiment of the present invention. As shown, the NAT database file, (the sequence file 159, in this example), can be viewed as a single flat file comprising a single long string.

The index file 160 comprises 4 fields. One index file is created for each physical flat file 159 that exists. The index file 160 thus comprises one entry for each locus in the associated flat file 159. The order of the entries in the index file 160 is the same order as the actual loci in the sequence file 159. The first field 162 in each index file 160 comprises the offset of the locus. Thus, the first entry has an offset of 0, following a header record (if any). The second entry has an offset of zero, plus the length of the first locus, and so on. The second field 163 in each entry comprises the length of the associated locus. This length includes the base text portion 4, the named portion 1, and the annotation portion 5 (i.e. the entire locus viewed as a single flat string of length L).

The third field 164 in each entry comprises the offset into the associated PSKEL file 170 (described below), associated with the particular locus. The last field 165 comprises the length of the associated PSKEL entry.

The PSKEL file 170 comprises an offset 172 and length 173 for every searchable object within the associated locus. Because different loci may comprise different elements, the number of records used to describe loci will vary. For example, a first locus may contain two REFERENCE sections and a second may contain only one. This is the reason why the length of each PSKEL entry is included in the associated index file 160.

Thus, as shown, a single PSKEL entry is associated with a single locus and comprises multiple records, wherein each record comprises information about one searchable object. In our example, the searchable objects include each of the sections, such as LOCUS 40 and DEFINITION 41, each sub-section, such as ORGANISM 50, and the base text or sequence section 54. Accordingly, offset 172 and length 172 information is listed for each searchable object.

Figure 14:
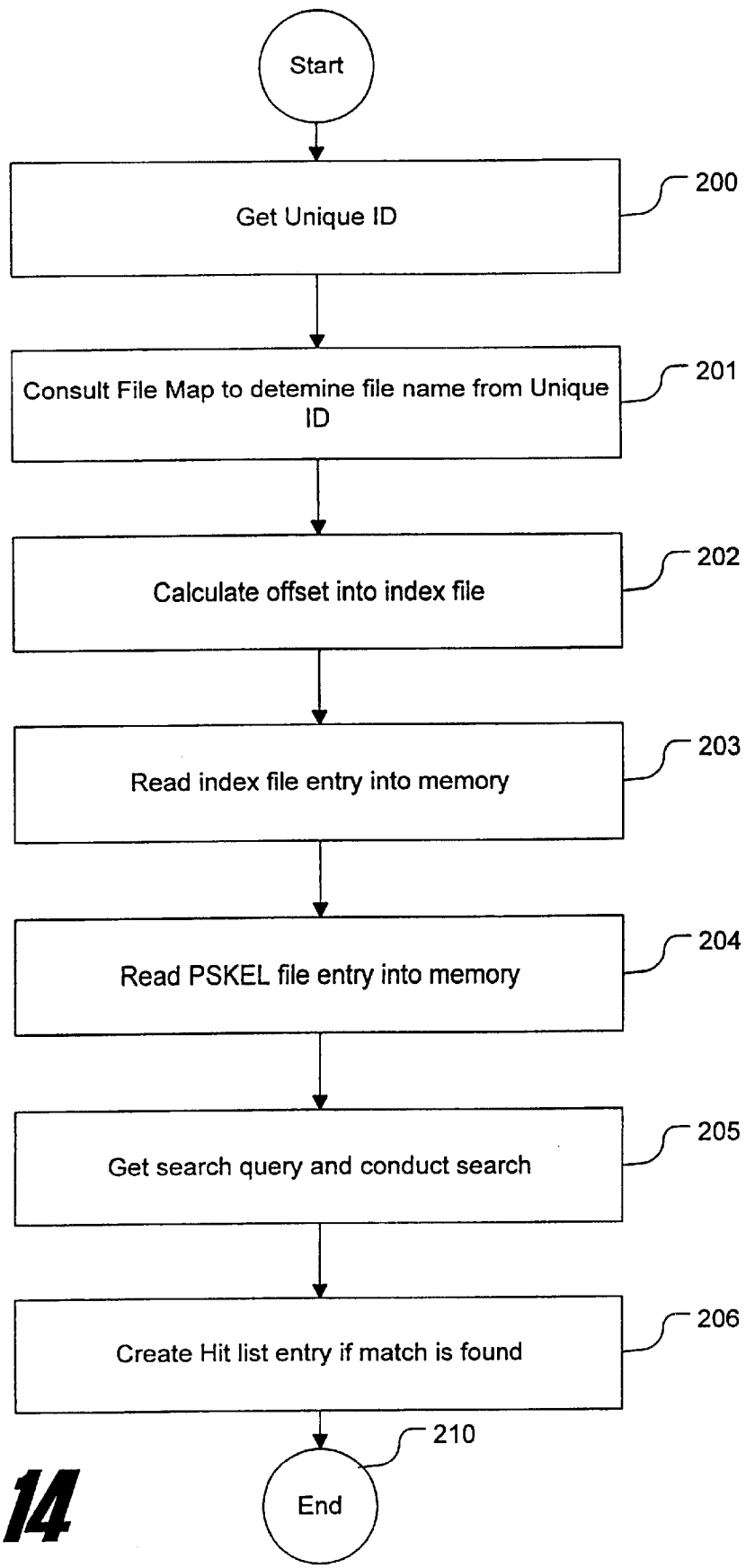
FIG. 14 is a flowchart depicting a process that can be used to implement the present invention.

FIG. 14 is a flowchart that depicts a process that can be used to prepare for a search in accordance with an embodiment of the present invention. The process begins with step 200, where a unique ID is retrieved. This can occur using several methods, two of which are described below.

Using a first method, the process receives a request to perform a search on a particular locus that is identified by name. In this case, the process reads the Global index file 140, and searches for the name provided. Once the name is found in the Global index file 140, the assigned unique ID is retrieved from that data record. In this example, it is assumed that the locus of interest is associated with the index file entry 150. Thus, it is determined that the locus of interest has a unique ID of 46,207.

More generally however, a search is initiated from a particular Hits list that comprises nothing more than an ordered list of unique IDs. For example, if a user is interested in performing a search on a bacterial database, the first step is to read the database, partition it, and create a Hits list therefrom. In this example, the Hits list would contain the unique ID of all of the loci in the bacterial part of the Genbank database. The other fields in the Hits list are generally set to zero. In any case, the first step to performing a search is to retrieve a unique ID associated with a particular locus.

Next, as indicated by step 201, the file map 143 is consulted to determine which file contains the particular locus of interest. In this example, it is determined that the unique ID 46,207 is stored in the second Genbank sequence file named: "BCT2.SEQ." Next, the process checks to see if the BCT2.SEQ file is open. If it is not, the current file is closed and the file "BCT2.SEQ" is opened.

Next, as indicated by step 202, the offset into the index file associated with the BCT2.SEQ file (typically named "BCT2.index") is calculated. This offset is simply calculated by subtracting the Unique ID 46,207, from the total number of loci appearing before it according to the file map. In this example, as shown in FIG. 12 (see 151) 40,716 loci are listed ahead of the BCT2.SEQ file. Thus, a simple calculation (46,207–40,716) yields a result of 5,491. Accordingly the locus to be searched is referenced by the $5491^{st}$ entry in the BCT2.index file.

Next, the header if any, in the BCT2.index file is skipped and the $5491^{st}$ record is retrieved, as indicated by step 203. As stated, this record comprises 4 fields, as shown by the index file 160. The first field 162 contains the offset into the Genbank file "BCT2.SEQ," where the particular locus is located. The second field 163 contains the length of the associated locus. The third field 164 contains the offset into the PSKEL file 170 (appropriately named BCT2.PSKEL). It should be recalled that the PSKEL file contains a road map pertaining to the searchable objects within the associated locus. The fourth field 165 contains the length of the entry in the PSKEL file 170. The PSKEL file is read into memory, as indicated by step 204.

Next, as indicated by step 205, the search query is read and the search is conducted. As noted, the first two fields from the index file in step 203 are used to read the actual locus data from the sequence file and the PSKEL file is used to determine exactly where to search for the requested keywords in the search query. The process ends as indicated by step 201.

The following example describes how a context search is performed in accordance with a preferred embodiment of the present invention. In this example, it is assumed that the context search described above with reference to FIG. 9 is being performed. Namely, the object of the context search is to find all possible instances of transcription factor binding sites (TFBS) in all Chicken sequence within the Genbank database. As stated above, the solution to this query is to search for instance of TFBS sequences, but only within a specified distance from each coding sequence (CDS). In specified distance used in this example is 500 bases "upstream" from each CDS.

The first task is to create a Hits list 98 (FIG. 9) containing all chicken sequences. A detailed view of a portion of the Hits list is shown as table 230 in FIG. 15. The numbers that appear on the left side of the table 230 (360–364) represent the index of the table 230. Thus, a line in the table 230 can be referenced by the index number. The other tables presented in FIG. and FIG. 18 are referenced in a similar manner.

It should be recalled that the Hits list 230 is the output from the first Search database module 91 which searches Genbank for those entries with an "Organism" value of "Gallus gallus." The Hits list 230 contains S hits that are numbered from 1 to S. The Search Hits list 230 is sorted in ascending order, with the iref field as the first key, the type field as the second and the mark field as the third key. Note that all mark fields are set to zero because this search is not a context search.

The next task is to search the Search Hits list 230 to find all sequences that have been identified as coding sequences (CDS). This step is represented by block 92 in FIG. 9. This is accomplished using a search of each entry's feature table 69 for features of type "CDS". The result is the Mark Hits list 99. A detailed view showing a portion of the Mark Hits list is shown as table 231 in FIG. 15. The Mark Hits table comprises M hits that are numbered from 1 to M. The preceding search is also a non-context search and as such, all mark fields are set to zero, as indicated.

The next task is to use the Search and Mark Hits lists, 230 and 231, respectively, as inputs into the context search (CS) module 95. Thus, the context searcher module 95 is presented with a Mark Hits list 231 numbered 1 to M, and a Search Hits list 230, numbered 1 to S. It is noted that M may be different than S.

Next, the Context Searcher 95 searches only those entries in the Search Hits list 230 that have an iref value that is also present in the Mark Hits list 231. This is so because there is no need to search any chicken entries that lacks coding sequences. This task is facilitated by the present invention because both tables 230 and 231 are sorted.

Thus, if the iref value of the Search Hits list 230 precedes the iref value of the current Mark Hits list 231, the process scans forward in the Search Hits list 230 and proceeds until either of the following three conditions occur:

1) the current iref value in the search Hit list 230 is equal to the iref of the current Mark Hits list 231, indicating that suitable context is present for this search hit; or
2) the iref value of the current Search Hits list 230 entry follows the iref value of the current entry of the Mark Hits list 231, in which case the Mark Hits list 231 will have to be advanced; or
3) the Search Hits list 230 is exhausted.

Alternatively, if iref value of the Mark Hits list 231 precedes the iref value of the current entry in the Search Hits list 230 than the process scans forward in the Mark Hits list 231 until either of the following three conditions occur:

1) its current iref is equal to that of the iref of the current Search Hits list 230; or
2) the iref value of the current Mark Hits list 231 follows that of the current Search Hits list 230 in which the Search Hits list 230 will have to be advanced; or
3) the Mark Hits list 231 is exhausted.

Thus the Context Searcher 95 works its way through both Hit lists 230 and 231, advancing whichever list with the iref that precedes the iref in the other list until:

1) a match is found; or
2) the next iref in the table that is being advanced follows that of the iref in the other table;
3) one (or both) tables is/are exhausted.

Note that when a match is detected, it may introduce a group of consecutive Hits in both the Mark Hits list 231 and/or the Search Hits list 230. In this case, the Context Search described below is performed for each search Hit using all of the relevant Mark Hits to establish context.

The results of this search, using the example lists in FIG. 15 (assuming these are the complete lists), are as follows. The Context Searcher 95 scans both tables to find the first entries with the same iref value, indicating that the CDS regions in the Mark Hits list 231 and the corresponding Search Hits list 230 refer to the same sequence. In this example the Mark Hits entry (index #99) has the same iref number 423 as does the Search Hits entry 230 (index #362).

Accordingly, the process continues in ascending order of the Mark Hits list 231 to discover if additional entries also have iref=423. In this case, the process finds the entries in the Mark Hits list 231 (index #100 and #101). Thus, a total of three CDS regions are found name in the Chicken sequence with iref=423.

Next, the context searcher loads the sequence corresponding to iref=423 as well as the addresses of the three CDS subsequences specified by entries #99, #100 and #101 of the Mark Hits list 231.

Figure 16:
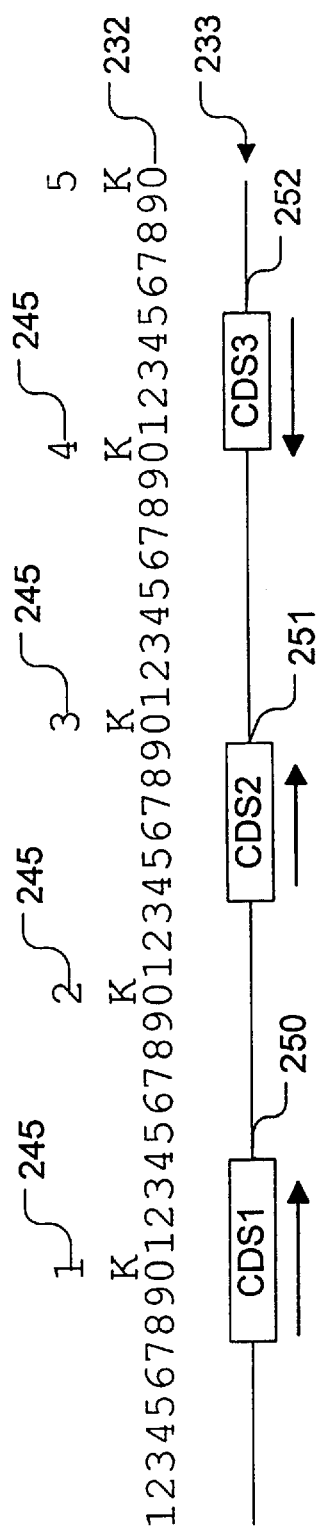
FIGS. 16 and 17 is a graphical depiction of a sequence showing context and target regions used to perform a context search in accordance with the present invention.
Figure 17:
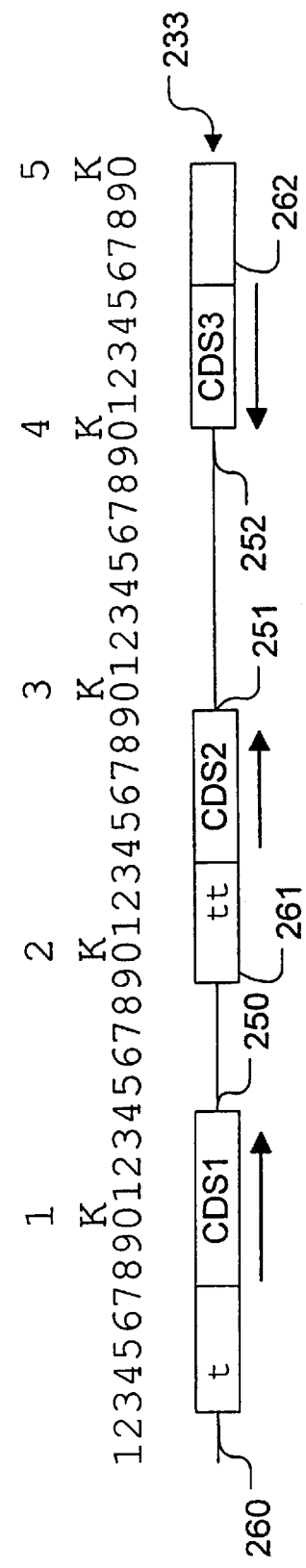

FIGS. 16 and 17 are diagrams that graphically depict these results. In FIG. 16, a sequence string having five thousand bases is represented by the horizontal line 233. The sequence data is numbered from one to five thousand as indicated by the numbering guide 232. The base markers 245 above the numbering guide (every thousand bases) indicate that each number in the numbering guide represents exactly 100 bases. Accordingly, FIGS. 16 and 17 depict:

A sequence 233 comprising 5000 base pairs numbered from left to right (1 to 5000).

The sequence 233 comprises three coding sequences (CDS) as follows:

1) CDS1 250 comprises 699 base pairs that are addressed from 801 to 1499. This coding sequence reads left to right, as indicated by the arrow beneath the CDS 1 250.
2) CDS2 (251) comprises 600 base pairs that are addressed from 2401 to 3000. This coding sequence reads left to right.
3) CDS3 (252) comprises 501 base pairs, from 4001 to 4501. This coding sequence is on the opposite strand as are CDS1 250 and CDS2 251. Accordingly, CDS3 252 reads from right to left, as indicated by the arrow.

Referring now to FIG. 17, the upstream regions of each coding sequence 250, 251 and 252 are represented by the rectangles 260 261 and 262, respectively. Thus, as shown, this sequence 233 has exactly three 500 base pair upstream regions that are each associated with a particular coding sequence as follows:

Region 260 (address: 301 to 800) comprises 500 bases upstream from CDS1 250;

Region 261 (address: 1901 to 2400) comprises 500 bases upstream from CDS2. 251; and Region 262 (address: 5000 to 4502) comprises 499 bases (the sequence ends) upstream from CDS3 252.

Note that CDS3 252 is on the complementary strand and is read right to left. Accordingly, the upstream region for CDS2 252 is to the right of the coding sequence.

The next task for the Context Searcher 95 is to limit the search for strings that are defined as transcription binding factor sites (TFBS) to the three sub-string regions 260, 261 and 262. A Hits list entry is generated for any match found in these regions. The Hits list entry includes an entry in the mark field that is set to the iref of the mark In this fashion, the Hit describes the context, in this example the corresponding CDS.

Continuing with the example, it is now assumed that the Context Searcher 95 finds three TFBS matches at the following positions: 400, 2100 and 2200. These matches are represented by the "t" in FIG. 17. Specifically, one match is found in the upstream region 260 of CDS 1 250, and two matches are found in the upstream region 261 of CDS2 251. In this example, no matches are found in the upstream region 262 of CDS3 252.

Referring now to FIG. 18, preliminary results Hits list 265 is used to temporarily store these results. The preliminary Hits list 265 is a table that contains RP entries. Note that the Mark Hits list 211 is reproduced in FIG. 18 for convenience to show the relationship between the preliminary results Hit list 265 and the Mark Hits list 211.

In particular, as shown, the mark field in the preliminary results Hits list 265 is used to store the index of the element from the Mark Hits list 265 that specifies the context associated with the resultant Hit.

Accordingly, as shown, the match (index #217) stored in the preliminary results Hits list 265 points to index #99 in the Mark Hits list 211. This indicates that the reported TFBS match (index #217) is associated with CDS1 250. Similarly, the match (index #218) stored in the preliminary results Hits list 265 points to index #100 in the Mark Hits list 211. This indicates that the reported ITBS match (index #218) is associated with CDS2 251. In addition, the match (index #219) stored in the preliminary results Hits list 265 also points to index #100 in the Mark Hits list 211. This indicates that the reported TFBS match (index #219) is also associated with CDS2 251.

The next task is to combine those elements from the Mark Hits list 211 that were actually used (i.e. those elements in which a TFBS match was found), with the Hits in a final Results Hits list 270. The final Results Hit List 270, is a Hit list of size RM that is the output from the Context Searcher 95.

As shown, the final results Hits list 270 comprises entries that represent context (i.e. index #s 177 and 178) and entries that represent matches (index #s179-181). The entries that represent matches (index #s 179–181), contain in their mark fields, the index numbers of the associated context entry within the same Hits list 270.

In a preferred embodiment, the numbers in the various Hits tables 211, 265 and 270 are represented in an unsigned binary format so that the lists can be sorted in accordance with the principals described above. In this fashion, the table can be sorted such that the most significant 8 bits are unaffected by the value of the marks (the least significant bits).

Thus, working backwards from the most common 32 bit word size, the largest mark is $2^{(24-1)}$ or 16,777,215. These unused bits can then be used to combine the two Hit lists 211 and 265 in a way that makes use of the fact that they are sorted into the same order.

This can be accomplished by using the following two functions named "GB_update_marks1( )" and GB_update_marks2( ) as follows:

RM=GB_update_marks1(M, MarkHits, mindex, RP, ResultHits);

GB_$_{update}$_marks2(mindex, RM, ResultHits);

The first function call returns the size of the results Hit list (RM), which is used in the second function call. The variable "mindex" is an integer array of size M, which is the size of the Mark Hits list 322.

The following tables contain pseudo-code that can be used to implement the GB_update_marks1 and GB_update_marks2 functions and related functions in accordance with a preferred embodiment of the present invention. In addition, macros and type definitions are included in a header file referred to as "Genbank.h," a part of which, is listed as pseudo-code in Table 5, below.

TABLE 3

GB_update_marks1

```
#include "genbank.h"
int  GB_update_marks1( n_mhits, mhits, mindex, n_hits, hits )
int  n_mhits
GB_HIT_T   mhits[ ];
int  mindex[ ];
int  n_hits
GB_HIT_T   hits[ ];
{
    int  i, m, mark;
    int  n_mindex;
    for( i = 0 i < n_hits; i++){
        if(( mark = GB_GET_HMARK( &hits[i])) == 0 )
            continue;
        mark--;
        if( GB_IS_HMARKER( &mhits[ mark ] ))
            continue;
        GB_SET_HMARKER( &mhits[ mark ] );
        for( m = GB_GET_HMARK( &mhits[ mark ] ); m; ){
            m++;
            if(GB_IS_HMARKER( &mhits[m ] ))
                break;
            GB_SET_HMARKER( &mhits[ m ] );
            m = GB_GET_HMARK( &mhits[ m ] );
        }
    }
    for( n_mindex = 0, m = 0; m < n_mhits; m++ ){
        if( GB_IS_HMARKER( &mhits[ m ] )){
            mindex[ m ] = n_mindex;
            n_mindex++;
        }else
            mindex[ m ] = -1;
    }
    for(i = 0; i < n_hits;i++){
        if(( mark = GB_GET_HMARK( &hits[i ] )) == 0 )
            continue;
        mark--;
        mark = mindex[ mark ];
        GB_SET_HMARK( &hits[ i ], mark + 1 );
    }
    for( m = 0; m < n_mhits;m++ ){
        if(( mark = GB_GET_HMARK( &mhits[ m ]))== 0 )
            continue;
        mark--;
        mark = mindex[ mark ];
        GB_SET_HMARK( &mhits[ m ],mark + 1 );
    }
    for( m = 0; m < n_mhits; m++ ){
        if( GB_IS_HMARKER( &mhits[ m ] )){
            hits[ n_hits ] = mhits[ m ];
            n_hits++;
        }
    }
    qsort( hits, n_hits, sizeof( GB_HIT_T ), GB_hitcmp );
    return( n_hits );
}
```

TABLE 4

GB_update_marks2

```
int  GB_update_marks2( mindex, n_hits, hits )
int  mindex[ ];
int  n_hits;
GB_HIT_T   hits[ ];
{
    int  i, m, mark;
    int  n_mindex;
    for( n_mindex = 0, i = 0; i < n_hits; i++ ){
        if( GB_IS_HMARKER( &hits[ i ])){
            mindex[ nmindex ] = i + 1;
            n_mindex++;
            GB_CLEAR_HMARKER( &hits[ i ]);
        }
    }
```

TABLE 4-continued

GB_update_marks2

```
for( i = 0; i < n_hits; i++){
    if(( mark = GB_GET_HMARK( &hits[ i ])) == 0)
            continue;
        mark--;
        GB_SET_HMARK( &hits[ i ], mindex[ mark ]);
    }
}
```

TABLE 5

Genbank.h

```
#define  GB_EOF           0
#define  GB_LOCUS         1
#define  GB_DEFINITION    2
#define  GB_ACCESSION     3
#define  GB_NID           4
#define  GB_VERSION       5
#define  GB_KEYWORDS      6
#define  GB_SEGMENT       7
#define  GB_SOURCE        8
#define  GB_ORGANISM      9
#define  GB_REFERENCE    10
#define  GB_AUTHORS      11
#define  GB_TITLE        12
#define  GB_JOURNAL      13
#define  GB_MEDLINE      14
#define  GB_REMARK       15
#define  GB_COMMENT      16
#define  GB_FEATURES     17
#define  GB_FEATURE      18
#define  GB_BASE_COUNT   19
#define  GB_ORIGIN       20
#define  GB_SEQUENCE     21
#define  GB_EOR          22
#define  GB_CONTINUE     23
#define  GB_NULL         24
#define  GB_ERROR        25
#define  GB_NSYMS        26
    /* Hit types - Must fit in 4 bits, 15 is largest! */
#define  H_LOCUS          0
#define  H_DEFINITION     1
#define  H_ACCESSION      2
#define  H_NID            3
#define  H_VERSION        4
#define  H_KEYWORDS       5
#define  H_ORGANISM       6
#define  H_REFERENCE      7
#define  H_FEATURES       8
#define  H_SEQUENCE       9
#define  H_CSEQUENCE     10
#define  H_FSEQUENCE     11
#define  H_NSYMS         12
    /* Hit subtypes for ref hits:     */
#define  HRP_ANY          0
#define  HRP_AUTHOR       1
#define  HRP_TITLE  2
#define  HRP_JOURNAL      3
#define  HRP_MEDLINE      4
#define  HRP_REMARK       5
    /* Hit actions - used by select_field:    */
#define  HA_ASIS          0
#define  HA_ADD           1
#define  HA_SUB           2
#define  GB_FMT_TEXT         0
#define  GB_FMT_TROFF        1
#define  GB_FMT_HTML         2
typedef  struct gb_hit_t     {
    unsigned int  h_iref;
    unsigned int  h_info;
    unsigned int  h_aux;
    unsigned int  h_mark;
} GB_HIT_T;
```

TABLE 5-continued

Genbank.h

```
/* macros for operating on hits:    */
#define  GB_GET_HMARK(hp)      ((hp)—>h_mark&0x0fffffff)
#define  GB_SET_HMARK(hp,m)    ((hp)—>h_mark=(((hp)—>h_mark&0xf0000000)|(m)))
#define  GB_IS_HMARKER(hp)     ((hp)—>h_mark&0x10000000)
#define  GB_SET_HMARKER(hp)    ((hp)—>h_mark|=0x10000000)
#define  GB_CLEAR_HMARKER(hp)  ((hp)—>h_mark&=~0x10000000)
```

Figure 19:
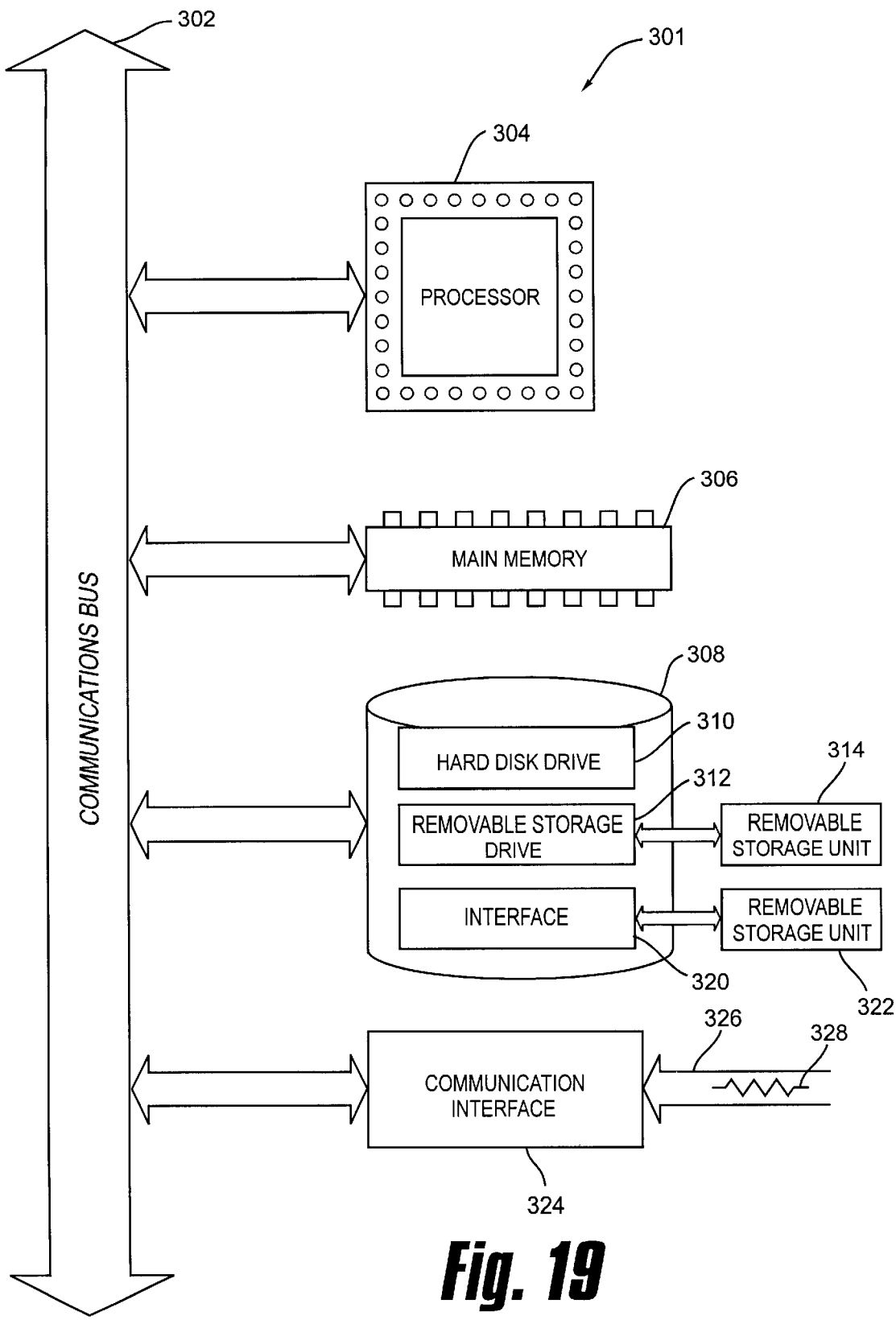
FIG. 19 is a block diagram depicting an exemplary computer system that can be used to implement various portions of the present invention.

The present invention may be implemented using hardware, software or a combination thereof and may be implemented in a computer system or other processing system. In fact, in one embodiment, the invention is directed toward a computer system capable of carrying out the functionality described herein. An example computer system 301 is shown in FIG. 19. The computer system 301 includes one or more processors, such as processor 304. The processor 304 is connected to a communication bus 302. Various software embodiments are described in terms of this example computer system. After reading this description, it will become apparent to a person skilled in the relevant art how to implement the invention using other computer systems and/or computer architectures.

Computer system 302 also includes a main memory 306, preferably random access memory (RAM), and can also include a secondary memory 308. The secondary memory 308 can include, for example, a hard disk drive 310 and/or a removable storage drive 312, representing a floppy disk drive, a magnetic tape drive, an optical disk drive, etc. The removable storage drive 312 reads from and/or writes to a removable storage unit 314 in a well known manner. Removable storage unit 314, represents a floppy disk, magnetic tape, optical disk, etc. which is read by and written to by removable storage drive 312. As will be appreciated, the removable storage unit 314 includes a computer usable storage medium having stored therein computer software and/or data.

In alternative embodiments, secondary memory 308 may include other similar means for allowing computer programs or other instructions to be loaded into computer system 301. Such means can include, for example, a removable storage unit 322 and an interface 320. Examples of such can include a program cartridge and cartridge interface (such as that found in video game devices), a removable memory chip (such as an EPROM, or PROM) and associated socket, and other removable storage units 322 and interfaces 320 which allow software and data to be transferred from the removable storage unit 322 to computer system 301.

Computer system 301 can also include a communications interface 324. Communications interface 324 allows software and data to be transferred between computer system 301 and external devices. Examples of communications interface 324 can include a modem, a network interface (such as an Ethernet card), a communications port, a PCM-CIA slot and card, etc. Software and data transferred via communications interface 324 are in the form of signals which can be electronic, electromagnetic, optical or other signals capable of being received by communications interface 324. These signals 326 are provided to communications interface via a channel 328. This channel 828 carries signals 326 and can be implemented using wire or cable, fiber optics, a phone line, a cellular phone link, an RF link and other communications channels.

In this document, the terms "computer program medium" and "computer usable medium" are used to generally refer to media such as removable storage device 312, a hard disk installed in hard disk drive 310, and signals 326. These computer program products are means for providing software to computer system 301.

Computer programs (also called computer control logic) are stored in main memory and/or secondary memory 308. Computer programs can also be received via communications interface 324. Such computer programs, when executed, enable the computer system 301 to perform the features of the present invention as discussed herein. In particular, the computer programs, when executed, enable the processor 304 to perform the features of the present invention. Accordingly, such computer programs represent controllers of the computer system 301.

In an embodiment where the invention is implemented using software, the software may be stored in a computer program product and loaded into computer system 301 using removable storage drive 312, hard drive 310 or communications interface 324. The control logic (software), when executed by the processor 304, causes the processor 304 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for searching a genetic sequence database comprising loci, each locus having a unique name, one or more annotations, and an ordered text string, the genetic sequence database being stored in one or more database files, the method comprising the steps of:

assigning a unique ID for each locus;

assigning an annotation identifier for each predefined annotation type;

constructing a parsed skeleton file associated with each of the database files, wherein each entry in the parsed skeleton file is associated with a particular locus and comprises one or more searchable object names, a length and an offset for each searchable object within the particular locus; and building an index file associated with each of the database files, wherein each entry in the index file comprises an offset and length into a database file for each locus and an offset and length of the corresponding entry in the parsed skeleton file.

2. The method of claim 1, further comprising the steps of:

selecting a portion of the genetic sequence database in which to conduct a search;

constructing an input hits list comprising the unique ID of each locus identified in said portion;

specifying a search key comprising one or more keywords and one or more annotation types;

performing a first database search using the input hits list and the search key; and outputting matches into a results hits list.

3. The method of claim 2, wherein said step of performing a first database search comprises the steps of:

reading the unique ID from the input hit list;

determining which of the one or more database files contains the unique ID;

calculating an offset into the associated index file, where the associated index entry is stored;

consulting the associated index entry to determine an offset and length of the locus and an offset and length of the associated parsed skeleton file entry;

reading the associated parsed skeleton file entry; and searching for a match of the search key using the parsed skeleton file to parse the locus.

4. The method of claim 3, further comprising the steps of:

presenting text associated with the results hits list to a user;

accepting input from the user for selecting one or more of the results;

converting the one or more of the results into one or more additional search keys; and performing a second database search using the search key from the first database search and the additional search keys.

5. The method of claim 3, wherein the results hits list comprises a unique multiple digit number representing each of the matches from said outputting step, wherein an entry in the results hits list comprises:

a first number in a first digit comprising the unique ID of the matched result; and a second number in a second digit comprising the annotation identifier of the matched result.

6. The method of claim 5, wherein the entry in the results hits list further comprises:

a third number comprising an offset of the ordered text string associated with the matched result; and a fourth number comprising a length of the ordered string associated with the matched result.

7. The method of claim 6, wherein the offset is appended to the second digit and the length is placed in a third digit of the multiple digit number.

8. The method of claim 5, wherein the entry in the results hits list further comprises a third number comprising an annotation order.

9. The method of claim 7, wherein the annotation order is stored in the most significant bits of a third digit and a zero is stored in the least significant bits of the third digit.

10. The method of claim 5, wherein said presenting step comprises the steps of:

constructing a results E-Hits list from the results hits list, wherein each element of the results E-Hits lists corresponds to a particular element in the results hits list and comprises:

string representation of the unique name corresponding to the unique ID;

string representation of the annotation type corresponding to the annotation identifier; and string representation of the value of the annotation or base text represented by the associated results hits list element.

11. A method for searching a genetic sequence database comprising a plurality of loci, each locus having a unique name, one or more annotations, and genetic sequence data represented as an ordered text string, the genetic database being stored in one or more database files, the method comprising the steps of:

assigning a unique ID for each locus;

assigning an annotation identifier for each predefined annotation type;

constructing a parsed skeleton file associated with each of the database files, wherein each entry in the parsed skeleton file is associated with a particular locus and comprises a length and offset for each of the annotations and the genetic sequence data within the particular locus;

building an index file associated with each of the database files, wherein each entry in the index file comprises an offset and length into a database file for each locus and an offset and length of the corresponding entry in the parsed skeleton file;

selecting a portion of the genetic database in which to conduct a search;

constructing an input hits list comprising the unique ID of each locus identified in said portion;

specifying a search key comprising one or more keywords and one or more annotation types;

performing a first database search using the input hits list and the search key; and outputting matches into a results hits list.

12. The method of claim 11, wherein said step of performing a first database search comprises the steps of:

reading the unique ID from the input hit list;

determining which of the one or more database files contains the unique ID;

calculating an offset into the associated index file, where the associated index entry is stored;

consulting the associated index entry to determine an offset and length of the locus and an offset and length of the associated parsed skeleton file entry;

reading the associated parsed skeleton file entry; and searching for a match of the search key using the parsed skeleton file to parse the locus.

13. The method of claim 12, further comprising the steps of:

presenting text associated with the results hits list to a user;

accepting input from the user for selecting one or more of the results;

converting the one or more of the results into one or more additional search keys; and performing a second database search using the search key from the first database search and the additional search keys.

14. A system for searching a genetic sequence database comprising loci, each locus having a unique name, one or more annotations, and an ordered text string, the genetic sequence database being stored in one or more database files, the system comprising:

a global index file generator coupled to the genetic sequence database for assigning a unique ID for each locus;

an annotation definition module coupled to the genetic sequence database for assigning an annotation identifier for each predefined annotation type;

a parsed skeleton file generator coupled to the genetic sequence database for constructing a parsed skeleton file associated with each of the database files, wherein each entry in the parsed skeleton file is associated with a particular locus and comprises one or more searchable object names, a length and an offset for each searchable object within the particular locus; and an index file generator coupled to the genetic sequence database for building an index file associated with each of the database files, wherein each entry in the index file comprises an offset and length into a database file for each locus and an offset and length of the corresponding entry in the parsed skeleton file.

15. The system of claim 14, further comprising:

a read database module coupled to the genetic sequence database for selecting a portion of the genetic sequence database in which to conduct a search and for constructing an input hits list comprising the unique ID of each locus identified in said portion; and a search module coupled to said read database module for specifying a search key comprising one or more keywords and one or more annotation types and for performing a first database search using said input hits list and said search key; and outputting matches into a results hits list.

16. The system of claim 15 further comprising:

a context hits list coupled to said read database module and defining a context in which to conduct a context search;

a target hits list coupled to said read database module for defining a target to search in a context search; and a context search module coupled to said context and target hits lists for searching said portion of the genetic sequence database for instances of targets defined by said target hits list in a context as defined by said context hits list and for constructing a results hits list therefrom.

17. The system of claim 16, wherein said results hits list comprises entries representing context and target matches, wherein said entries representing target matches include a pointer to an entry representing the relevant context.

18. A method for performing a context search on a genetic sequence database comprising loci, each locus having a unique name, one or more annotations, and an ordered text string, the genetic sequence database being stored in one or more database files, the method comprising the steps of:

reading an ordered string;

partitioning the ordered string into a plurality of substrings each marked either target or context;

specifying one or more context relationships;

searching for sub-strings marked target within regions that satisfy the specified context relationships;

storing matches found in said searching step; and marking each sub-string found in said searching step with its associated context;

wherein said storing and marking steps comprise the steps of:

creating a results hits list comprising an array wherein each entry of the array comprises an iref number, a type field, and mark field;

storing a pointer within each mark field that points to the associated context reference entry.

19. A computer program product comprising a computer useable medium having computer program logic stored therein, said computer program logic for enabling a computer to perform a context search on a genetic sequence database comprising loci, each locus having a unique name, one or more annotations, and an ordered text string, the genetic sequence database being stored in one or more database files, wherein said computer program logic comprises:

read means for enabling the computer to read an ordered string;

partition means for enabling the computer to partition the ordered string into a plurality of sub-strings each marked either target or context;

means for enabling the computer to specify one or more context relationships;

searching means for enabling the computer to search for sub-strings marked target within regions that satisfy the specified context relationships;

storage means for enabling the computer to store matches found in said searching step;

means for enabling the computer to mark each sub-string found in said searching step with its associated context;

means for enabling the computer to create a results hits list comprising an array, wherein each entry of the array comprises an iref number, a type field, and a mark field; and means for enabling the computer to store a pointer within each mark field that points to the associated context reference entry.

20. A method for searching a genetic sequence database, the database comprising loci, each locus having a unique name, one or more annotations, and an ordered text string, the database being stored in one or more database files, the method comprising the steps of:

constructing a file map for the database, said file map comprising the file name of each database file in the database and the number of loci within each file;

constructing a global index comprising the names of all the loci and a unique ID for each locus;

building a parsed skeleton file associated with each database file, said parsed skeleton file comprising a plurality of entries, each entry associated with an individual locus, wherein each entry comprises one or more searchable object names, and an offset and length for each searchable object with a locus;

building an index file associated with each database file, said index file comprising a plurality of entries, each entry associated with an individual locus, wherein each entry comprises an offset into a database file, a length of the locus, an offset into the corresponding parsed skeleton file, and a length of the parsed skeleton file;

retrieving a unique ID associated with a particular locus of interest;

consulting the file map to determine the database file that contains the particular locus of interest;

calculating the offset into said index file associated with said database file;

reading the index file entry and the parsed skeleton file entry into memory; and reading a first search query and conducting a first database search.

21. A method according to claim 20, wherein the genetic sequence database is a GENBANK database.

22. A method according to claim 20, further comprising the step of creating a hits list.

23. A method according to claim 20, further comprising the step of creating a results hits list.

24. A method according to claim 23, further comprising the steps of:

presenting text associated with the results hit list to a user;

accepting input from the user for selecting one or more of the results;

converting the one or more results into one or more additional search queries; and performing a second database search using the search query from the first database search and the additional one or more search queries.

25. A method according to claim 20, further comprising the step of assigning an annotation identifier for each predefined annotation type, said assigning step occurring prior to the first database search.

26. A method according to claim 25, wherein the first search query of the first database search comprises one or more keywords and one or more annotation types.

* * * * *

UNITED STATES PATENT AND TRADEMARK OFFICE
CERTIFICATE OF CORRECTION

PATENT NO. : 6,249,784 B1
DATED : June 19, 2001
INVENTOR(S) : Macke et al.

It is certified that error appears in the above-identified patent and that said Letters Patent is hereby corrected as shown below:

Title page,
Item [75], please change the inventor's name from "Bill F. Butler" to
-- William F. Butler --.
Item [56], References Cited, OTHER PUBLICATIONS, please change "Dr" to -- Dr. -- and "199(6)" to -- 119(6) --.

Column 2,
Line 4, change "is part" to -- in part --.

Column 3,
Lines 50 and 53, change "forth" to -- fourth --.

Column 4,
Line 62, change "is" to -- are --.

Column 5,
Line 18, change "is" to -- are --.
Line 36, change "An" to -- A --.

Column 7,
Line 16, change "0" and "4" to -- 0 -- and -- 4 --.
Lines 41 and 42, change "target (s)" to -- target(s) --.
Line 66, change "sub strings" to -- sub-strings --.

Column 8,
Line 23, change "module 23" to -- module 22 --.

Column 9,
Line 10, change "annotations" to -- annotation --.
Line 45, change "substrings" to -- sub-strings --.

Column 10,
Lines 20, 23, 26, 27, 52 and 54, change "Ehits" to -- E-hits --.

Column 12,
Line 23, change "CDS 48" to -- CDS 68 --.
Line 24, change "REFERECE" to -- REFERENCE --.
Line 25, change "41 and 43" to -- 48 and 49 --.
Line 30, change "know" to -- known --.

UNITED STATES PATENT AND TRADEMARK OFFICE
CERTIFICATE OF CORRECTION

PATENT NO. : 6,249,784 B1
DATED : June 19, 2001
INVENTOR(S) : Macke et al.

It is certified that error appears in the above-identified patent and that said Letters Patent is hereby corrected as shown below:

Column 13,
Line 1, change "ORGANISM 40'" to -- ORGANISM 60 --.
Line 47, change "substring" to -- sub-string --.
Line 59, change "column 22" to -- column 22 --.

Column 14,
Line 25, change "41" to -- 48 --.
Line 27, change "43" to -- 49 --.

Column 15,
Lines 4, 10 and 18, change "41 and 43" to -- 48 and 49 --.
Line 39, change "(A)" to -- (^) --.
Line 64, change "$>$" to -- $\geq$ --.

Column 16,
Lines 7, 9, and 16, change "$\geqq$" to -- $\geq$ --.
Line 44, change "forth" to -- fourth --.

Column 18,
Line 28, change "70" to -- 80 --.
Line 55, change "(E)" to -- (H) --.

Column 19,
Lines 4, 13 and 23, change "88" to -- 78 --.
Line 53, change "sequence," to -- sequence. --.
Lines 63 and 65, change "tt's" to -- ttt's --.

Column 20,
Line 6, change "48" to -- 68 --.
Line 16, change "unknown"" to -- "unknown" --.
Line 50, change "41 and 43" to -- 48 and 49 --.

Column 21,
Line 28, change "81" to -- 91 --.
Line 32, change "module" to -- module 94 --.

UNITED STATES PATENT AND TRADEMARK OFFICE
CERTIFICATE OF CORRECTION

PATENT NO.    : 6,249,784 B1
DATED         : June 19, 2001
INVENTOR(S)   : Macke et al.

It is certified that error appears in the above-identified patent and that said Letters Patent is hereby corrected as shown below:

Column 22,
Line 22, change ""BCTI.SEQ"" to -- "BCT1.SEQ" --.

Column 23,
Line 43, change "50" to -- 60 --.
Line 44, change "172" to -- 173 --.

Column 24,
Line 40, change "201" to -- 210 --.
Line 59, change "FIG. and" to -- FIG. 15 and --.

Column 25,
Line 29, change "search" to -- Search --.
Line 67, change "423" to -- 423 --.

Column 26,
Line 13, change "233" to -- 233 --.
Line 48, change "252" to -- 251 --.

Column 27,
Line 6, change "265" to -- 211 --.
Line 28, change "results" to -- Results --.
Line 50, change "GB_update_marks2()" to -- GB_update_marks2() --.
Line 54, change "$_{update}$" to -- update --.
Line 59, change "322" to -- 211 --.

Column 28,
Line 13, indent "for(i=0I<n_hits;i++){"
Line 20, change "m++" to -- m-- --.

UNITED STATES PATENT AND TRADEMARK OFFICE
CERTIFICATE OF CORRECTION

PATENT NO. : 6,249,784 B1
DATED : June 19, 2001
INVENTOR(S) : Macke et al.

It is certified that error appears in the above-identified patent and that said Letters Patent is hereby corrected as shown below:

Column 31,
Line 26, change "302" to -- 301 --.
Line 62, change "828" to -- 328 --

Signed and Sealed this

Tenth Day of September, 2002

Attest:

JAMES E. ROGAN
Attesting Officer
Director of the United States Patent and Trademark Office